(12) United States Patent
James et al.

(10) Patent No.: US 10,753,838 B2
(45) Date of Patent: Aug. 25, 2020

(54) SYSTEMS AND METHODS FOR VERIFICATION AND CALIBRATION OF HAMBURG WHEEL TRACKER DEVICES

(71) Applicant: InstroTek, Inc., Raleigh, NC (US)

(72) Inventors: Lawrence James, Raleigh, NC (US); Ali Regimand, Raleigh, NC (US); Ethan Steckmann, Durham, NC (US); Richard Stacy, Fayetteville, NC (US); Dirk Steckmann, Raleigh, NC (US); Andrew LaCroix, Raleigh, NC (US); Adam O'Neill, Durham, NC (US)

(73) Assignee: InstroTek, Inc., Research Triangle Park, NC (US)

( * ) Notice: Subject to any disclaimer, the term of this patent is extended or adjusted under 35 U.S.C. 154(b) by 217 days.

(21) Appl. No.: 16/038,350

(22) Filed: Jul. 18, 2018

(65) Prior Publication Data
US 2019/0025168 A1    Jan. 24, 2019

Related U.S. Application Data

(60) Provisional application No. 62/533,815, filed on Jul. 18, 2017.

(51) Int. Cl.
*G01N 3/00* (2006.01)
*G01N 3/02* (2006.01)
(Continued)

(52) U.S. Cl.
CPC ............ *G01N 3/02* (2013.01); *G01N 3/42* (2013.01); *G01N 3/56* (2013.01); *G01N 33/42* (2013.01); *G01N 2203/0682* (2013.01)

(58) Field of Classification Search
CPC .. G01N 2203/0682; G01N 33/42; G01N 3/02; G01N 3/42; G01N 3/56; G01N 3/00; G01N 11/00
See application file for complete search history.

(56) References Cited

U.S. PATENT DOCUMENTS 3,459,038 A  *  8/1969  Swift ................. G01C 7/04
                                                    73/146
4,788,859 A  *  12/1988  Khattak ............. G01B 11/16
                                                    356/624
(Continued)

OTHER PUBLICATIONS

Aschebrener T. et al., "Comparison of the Hamburg Wheel-Tracking Device and the Environmental Conditioning System to Pavements of Known Stripping Performance", U.S. Department of Transportation Federal Highway Administration, Jan. 1994, 108 pages.
Aschenbrener T., Evaluation of Hamburg Wheel-Tracking Device to Predict Moisture Damage in Hot-Mix Asphalt, Transportation Research Record 1492, (1995) pp. 193-201.
(Continued)

*Primary Examiner* — Francis C Gray
(74) *Attorney, Agent, or Firm* — Myers Bigel, P.A.

(57) ABSTRACT

A load and motion measurement system for use with a Hamburg Wheel Tracker device includes: a housing; at least one load cell held in or by the housing; a load platform held in or by the housing and resting on the at least one load cell; and a controller operatively associated with the at least one load cell. The load and motion measurement system is configured to be received in a sample tray that is held in the Hamburg Wheel Tracker device. The controller is configured to determine operational parameters associated with a wheel of the Hamburg Wheel Tracking device that rolls along the load platform. Vertical displacement measurement calibration and verification systems for use with a Hamburg Wheel Tracker device are also described, as are associated kits and methods.

20 Claims, 17 Drawing Sheets

(51) Int. Cl.
*G01N 33/42* (2006.01)
*G01N 3/56* (2006.01)
*G01N 3/42* (2006.01)

(56) References Cited

U.S. PATENT DOCUMENTS

| | | | | |
|---|---|---|---|---|
| 5,659,140 | A * | 8/1997 | Jakob | G01N 3/56 73/788 |
| 5,773,496 | A | 6/1998 | Grubba | |
| 5,795,929 | A | 8/1998 | Grubba | |
| 5,969,261 | A * | 10/1999 | McAlister | G01N 33/42 73/146 |
| 5,987,961 | A * | 11/1999 | Harris | G01N 3/56 73/11.01 |
| 6,125,685 | A * | 10/2000 | Collier | G01N 3/56 73/146 |
| 7,082,839 | B2 * | 8/2006 | Pyle | G01N 3/56 73/808 |
| 8,376,729 | B2 * | 2/2013 | Manbrini | G01N 3/32 425/374 |
| 9,964,471 | B2 * | 5/2018 | Regimand | G01N 1/28 |
| 2019/0323933 | A1 * | 10/2019 | Saleh | G01N 3/34 |

OTHER PUBLICATIONS

Eurekalert "Hand-portable device detects biological agents", American Society for Microbiology, Public Release: Mar. 11, 2003, Retrieved from the internet on Aug. 13, 2015 at URL http://www.eurekalert.org/pub_releases/2003-03/asfm-hdd030703.php.

Federal Highway Administration Research and Technology, Bituminous Mixtures Laboratory, Apr. 13, 2014, Retrieved from the internet on Aug. 13, 2015 at URL http://www.fhwa.dot.gov/research/tfhrc/labs/materialscomplex/mixtures/.

Federal Highway Administration, Bituminous Mixtures Laboratory, Hamburg Wheel-Tracking Device, Feb. 10, 1997, pp. 266-271.

Gundry et al. "Amplicon Melting Analysis with Labeled Primers: A Closed-Tube Method for Differentiating Homozygotes and Heterozygotes", Clinical Chemistry, 49:3, pp. 396-406 (2003).

Izzo R. et al., "Evaluation of the Use of the Hamburg Wheel-Tracking Device for Moisture Susceptibility of Hot Mix Asphalt", Texas Department of Transportation, Feb. 26, 1999, 25 pages.

Park T., Lovell C.W., "Using Pyrolized Carbon Black From Waste Tires in Asphalt Pavement", Purdue University, School of Engineering, Indiana Department of Transportation, Joint Highway Research Project, Feb. 20, 1996, 350 pages.

AASHTO Designation: T 324-11, "Hamburg Wheel-Track Testing of Compacted Hot Mix Asphalt", Nov. 2011, 10 pages.

* cited by examiner

SYSTEMS AND METHODS FOR VERIFICATION AND CALIBRATION OF HAMBURG WHEEL TRACKER DEVICES

RELATED APPLICATIONS

This application claims priority from U.S. Provisional Application No. 62/533,815, filed Jul. 18, 2017, the disclosure of which is incorporated by reference in its entirety.

BACKGROUND

Asphalt concrete mixture is the most frequently used material for building roads. Asphalt concrete is a mixture of asphalt binder and aggregates. The mixture is designed by adjusting the quantity of asphalt binder to balance two common distresses: rutting and cracking. Rutting is the formation of depressions in the pavement in the direction of the traffic flow caused by repeated wheel loadings. If the percentage of asphalt binder is too low, the mixture is prone to cracking. If the percentage of asphalt binder is too high, the mixture is prone to rutting.

Loaded wheel tracking devices have been used in the asphalt industry to determine pavement mixture design rutting performance in the laboratory by simulating a vehicle wheel rolling over a sample of asphalt mixture. These devices apply a weight to a wheel—either by dead weight or applied weight using a pneumatic system—that travels back and forth on a sample of compacted asphalt mixture. If the mixture is not designed properly with the right combination of aggregates, aggregate gradation, and binder content, the samples will rut prematurely. The wheel tracking test allows designers and practitioners to adjust the mixture to meet the requirements of the pavement conditions, including the environment and traffic load.

One of wheel-tracking tests is described in the AASHTO T324 standard and is known in the industry as the Hamburg Wheel-Tracking (HWT) test. Referring to FIG. 1, in a typical HWT test, two cylindrical asphalt mixture samples 12 are cut to form a continuous surface. The samples 12 are placed in a tray 10 and surrounded by plastic molds 14 to maintain their circular shape during testing and then are placed in 50° C. water. The samples 12 and the molds 14 are held within a sample compartment 16. The samples 12 are loaded with a wheel load of 703 N (158 lbf). More specifically, the samples 12 are loaded into a Hamburg Wheel Tracker device such as the Hamburg Wheel Tracker device 50 illustrated in FIG. 2. The Hamburg Wheel Tracker device 50 includes one or more (typically two) load arm assemblies 52. Each load arm assembly 52 includes a wheel 54 as shown in FIG. 3. The wheel 54 passes back and forth over the samples 12 as indicated by the arrow 56 in FIG. 3. The test is performed to a maximum of 20,000 passes of the wheel over the specimens or until a vertical deformation of 12.5 mm is recorded Hamburg Wheel Tracker devices and HWT tests are described in more detail in U.S. Patent Application Publication No. 2015/0292989, the disclosure of which is incorporated by reference in its entirety.

Hamburg Wheel Trackers currently used in the industry have four distinct actions that are verified to meet the equipment requirements of the standard: the load applied to the sample, the measurement of the vertical displacement of the wheel as the sample ruts, the temperature of the sample conditioning environment, and the horizontal displacement, velocity, and waveform pattern of the wheel along the wheel path. Because asphalt mixture is sensitive to load and temperature, these values must be accurately measured.

Load, vertical displacement, and temperature can be measured using equipment such as calibrated load cells, height blocks, and temperature devices, respectively, but such equipment requires considerable effort such as lifting weights over 100 lbs to place the load cell beneath the wheel as well as removing the displacement measurement devices from the Hamburg Wheel Tracker device.

Perhaps the most difficult part of complying with the test standard is verifying the correct horizontal motion of the wheel because this is a dynamic process and cannot be performed with the wheel in one position like the load and vertical displacement measurements. The verifications include the goodness of fit of horizontal wheel movement to a sinusoidal shape, the speed of the wheel at the center of motion, the period of motion, and the amplitude of the motion or the distance traveled. The horizontal motion is important to ensure even loading of the samples or specimens so results can be accurately compared between laboratories. Also, the center of motion of the load should be symmetrical over the two specimens being loaded. The interface or joint between the two specimens can be a weakened area that generally ruts more than other areas. Therefore, the vertical displacement system should be aligned with this interface to accurately measure the displacement at this critical position.

SUMMARY

Some embodiments of the invention are directed to a kit for calibrating and verifying the proper operation of a Hamburg Wheel Tracking device includes a load and motion measurement system and a vertical displacement measurement calibration and verification system. The load and motion measurement system includes: a housing; at least one load cell held in or by the housing; a load platform held in or by the housing and resting on the at least one load cell; and a controller operatively associated with the at least one load cell. The calibration of the load measurement system is critical to the correct operation of the system and may be accomplished at the manufacturer's facility or on-site by using special equipment which may include but is not limited to a spring loading system, a dead weight system, or a lever loading mechanism. The load and motion measurement system is configured to be received in a sample tray that is held in the Hamburg Wheel Tracker device. The controller is configured to determine operational parameters associated with a wheel of the Hamburg Wheel Tracking device that rolls along the load platform. The vertical displacement measurement calibration and verification system includes: a frame; and a plurality of height blocks configured to be selectively stacked on the frame. The frame is configured to be received in a sample tray that is held in the Hamburg Wheel Tracker device such that a wheel thereof rolls onto the frame and/or one or more of the height blocks stacked thereon to verify the accuracy of a vertical displacement device associated with the Hamburg Wheel Tracker device.

Some other embodiments of the invention are directed to a load and motion measurement system for use with a Hamburg Wheel Tracker device. The system includes: a housing; at least one load cell held in or by the housing; a load platform held in or by the housing and resting on the at least one load cell; and a controller operatively associated with the at least one load cell. The load and motion measurement system is configured to be received in a sample tray that is held in the Hamburg Wheel Tracker device. The controller is configured to determine operational parameters associated with a wheel of the Hamburg Wheel Tracking device that rolls along the load platform.

Some other embodiments of the invention are directed to a vertical displacement measurement calibration and verification system for use with a Hamburg Wheel Tracker device. The system includes: a frame; and a plurality of height blocks configured to be stacked on the frame. The frame is configured to be received in a sample tray that is held in the Hamburg Wheel Tracker device such that a wheel thereof rolls onto the frame and/or one or more of the height blocks stacked thereon to verify the accuracy of a vertical displacement measurement device associated with the Hamburg Wheel Tracker device.

Some other embodiments of the invention are directed to a method for calibrating and verifying the proper operation of a Hamburg Wheel Tracking device. The method includes providing a load and motion measurement system comprising. The load and motion measurement system includes: a housing; at least one load cell held in or by the housing; and a load platform held in or by the housing and resting on the at least one load cell. The method includes: installing the load and motion measurement system in a sample tray; installing the sample tray holding the load and motion measurement system in the Hamburg Wheel Tracker device; operating the Hamburg Wheel Tracking device such that a wheel thereof oscillates over the load platform a plurality of times; and using a controller in communication with the load and motion measurement system, outputting operational parameters associated with the oscillating wheel of the Hamburg Wheel Tracking device.

Some other embodiments are directed to a method for calibrating and verifying the proper operation of a Hamburg Wheel Tracking device. The method includes providing a vertical displacement measurement verification system. The vertical displacement measurement verification system includes: a frame; and a plurality of blocks in a stack having first height on the frame. The method includes: installing the vertical displacement measurement verification system in a sample tray; installing the sample tray holding the vertical displacement measurement verification system in the Hamburg Wheel Tracker device; operating the Hamburg Wheel Tracker device such that the wheel thereof rolls onto and rests on the stack of blocks on the frame; and comparing a vertical displacement measurement from the Hamburg Wheel Tracker device with the first height of the stack of blocks on the frame.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE FIGURES

FIG. 10 also illustrates the use of end spacers to help hold the system in the sample tray.

FIG. 20 also illustrates the use of end spacers to help hold the system in the sample tray.

DETAILED DESCRIPTION

Figure 1:
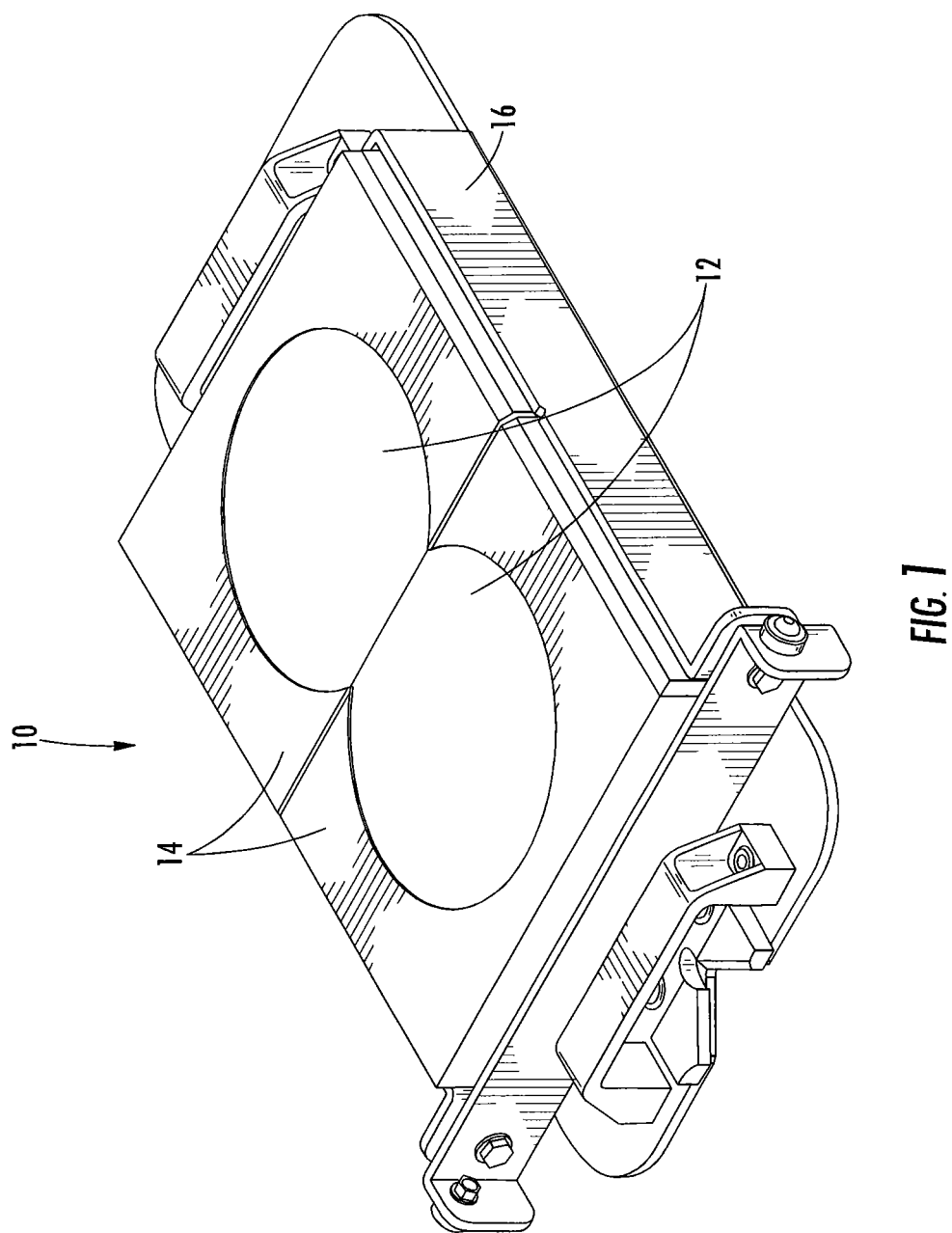
FIG. 1 is a perspective view illustrating a typical sample or specimen tray with samples or specimens held therein for performing the HWT test.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the expression "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Embodiments of the present invention provide systems and method for the verification and/or calibration of the operational parameters of wheel tracker devices. As used herein, "verification" means using a reference and comparing the operational parameters of the wheel tracker device to the reference to determine if the device is within specified tolerances. As used herein, "calibration" means in addition to verification a possible adjustment of the device and/or operational parameters, then a subsequent verification to determine if the operational parameters after adjustment of the system meet defined specifications. Embodiments of the present invention comprise a kit with a plurality of measurement systems, two or more of which may be included in a kit: a load and motion measurement system, a vertical displacement measurement system, and a temperature measurement system. As described in more detail below, the load and motion measurement system may be placed into the sample tray and aligned using spacer blocks designed for that particular manufacturer. The sample tray and the load and motion measurement system may then be placed into the wheel tracker. The parameters that can then be verified include one or more of the applied load, the stroke of the wheel, the center of motion of the wheel, the speed of the wheel at center, the dynamic load of the wheel, and a comparison of the measured waveform of the wheel position with a theoretical waveform. The data from the motion and load measurement system may be transferred to data storage either through a connecting cable or a wireless connection. As described in more detail below, the vertical displacement measurement system is designed to fit into the sample trays analogous to load and motion measurement system and may use the same spacer blocks. It can verify and/or calibrate the vertical displacement measuring system of the wheel tracker device. In addition, the vertical displacement measurement system can have the capability of verifying and/or calibrating the vertical displacement measurement transducer outside the wheel tracker.

Figure 4:
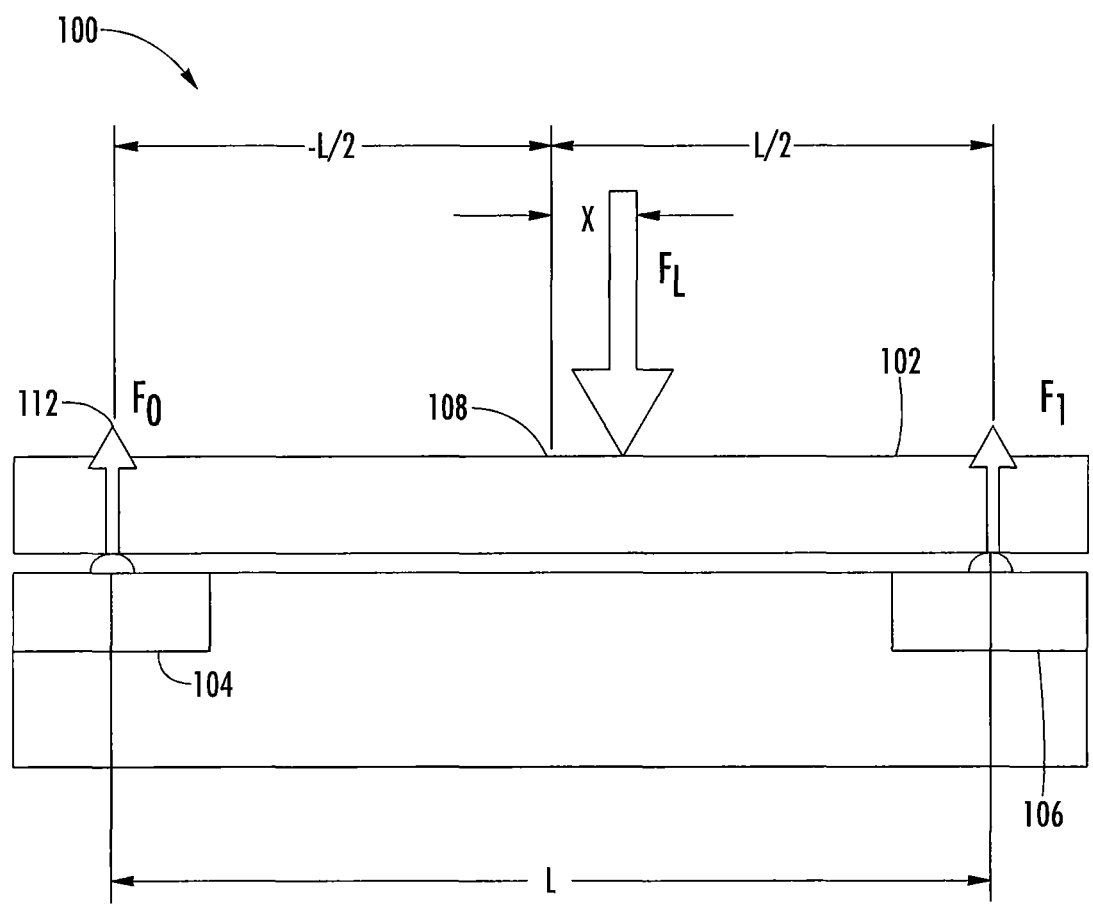
FIG. 4 schematically illustrates a load and motion measurement system including load cells according to some embodiments and the relationship between the forces on the load cells and the loading force.

FIG. 4 schematically illustrates a load and motion measurement system 100 for measuring load and displacement of a wheel of a Hamburg Wheel Tracker device. The load $F_L$ is applied to a loading platform 102 between first and second load cells 104 and 106. As illustrated, the load $F_L$ is applied at a position x just to the right of the midpoint 108 between of the load cells 104, 106. The load $F_L$ on the platform 102 will be the sum of load $F_0$ experienced on load cell 104 and the load $F_1$ experienced on load cell 106 as shown in equation (1) below.

$$F_L = F_0 + F_1 \quad (1)$$

The position x from the center or midpoint 108 between the load cells 104 and 106 can be calculated by forming the difference of the load $F_1$ on load cell 106 and the load $F_0$ on load cell 104, dividing that difference by the load $F_L$, and multiplying the quantity by length L (where L may be the actual length or a calibrated length) between the load cells 104, 106 divided by 2. This is shown in equation (2) below.

$$x = \frac{L}{2}\left(\frac{F_1 - F_0}{F_L}\right) \quad (2)$$

It can be seen that if the load is entirely situated on load cell 104 then the load on load cell 104 is equal to the load $F_L$ and the load on load cell 106 is zero, resulting in displacement of −L/2. Likewise, if the load is entirely situated on load cell 106 then the load on load cell 106 is equal to the load $F_L$ and the load on load cell 104 is zero, resulting in a displacement of +L/2. As mentioned above, the load is measured by adding the load $F_0$ on load cell 104 to the load on $F_1$ on load cell 106. Load data may be accumulated across the total displacement L or length between the load cells 104, 106 to verify that the load $F_L$ is the same or about the same at each position.

Figure 5:
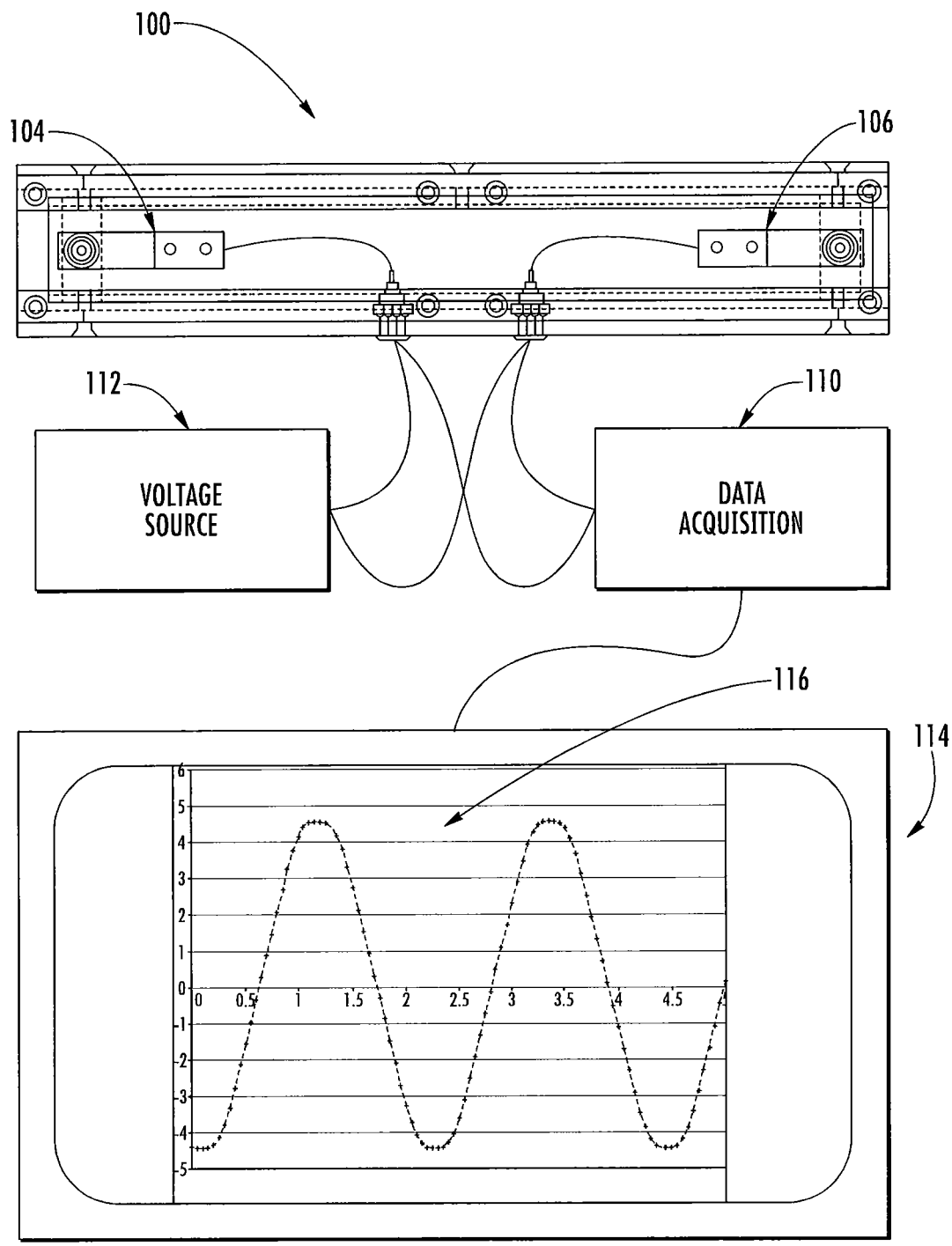
FIG. 5 schematically illustrates the placement of the load cells relative to each other in the system of FIG. 4 along with connections for data acquisition and a schematic of captured data.

FIG. 5 schematically illustrates the load and motion measurement system 100 according to some embodiments including a data acquisition system 110. Load cell 104 and load cell 106 may be coupled or connected to voltage source 112. In addition, load cell 104 and load cell 106 may be coupled or connected to the data acquisition system 110. Data may be collected by computer, processor and/or controller 114 having or communicating with a display 116 that may display the data (or data processed by the computer, processor and/or controller 114).

According to some other embodiments, the load and motion measurement system 100 may be configured with the voltage source 112 to the load cells and/or additional electronics or electronic circuit embedded in the housing that contains load cells 104 and 106. The electronics or electronic circuit may communicate wirelessly with the data acquisition system 110 and/or the controller 114.

Figure 6:
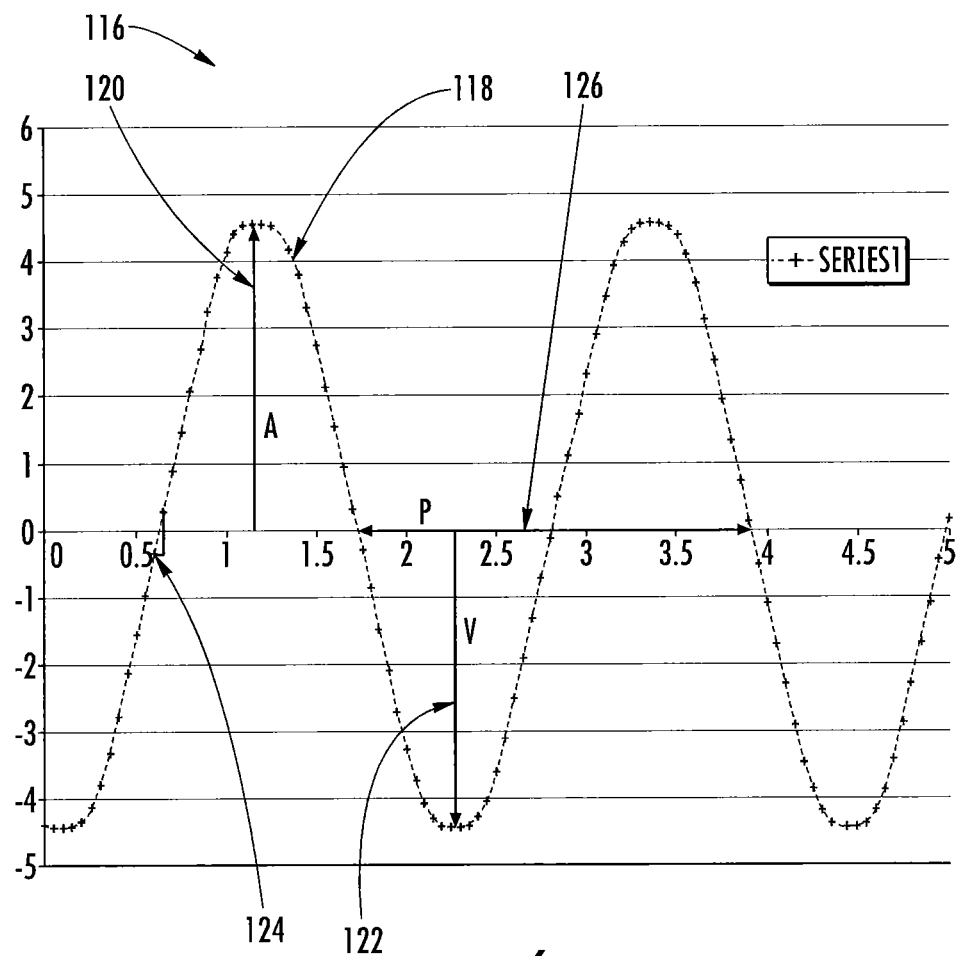
FIG. 6 is a graph used to describe the nomenclature of the captured loading waveform using the system of FIG. 4.

FIG. 6 shows the measurement parameters that may be obtained from analysis of the dynamic horizontal wheel motion data (e.g., the data that may be displayed on the display 116). The data points collected by the data acquisition system 110 (FIG. 5) along with the lines connecting the data points are illustrated at 118, where the displacement values along the vertical axis are shown plotted against time along the horizontal axis. Callout 120 shows the positive amplitude of the waveform generated from equation (2) above, and callout 122 shows the negative amplitude generated from equation (2) above from which the stroke may be obtained by adding the absolute values of 120 and 122. The difference in the absolute values of 122 from 120 provides the deviation of the wheel away from the center of travel (ideally in the symmetric case that deviation would be zero). The sign (e.g., positive or negative) will indicate which direction the deviation occurs. In addition, callout 124 shows that the speed of the wheel across the center of the device may be determined by calculating the slope of the displacement time curve as it crosses zero. Also, callout 126 shows that the period P may be determined by measuring the time of a first zero crossing and measuring the time of a second zero with a slope of the same sign crossing after the first zero crossing.

Figure 7:
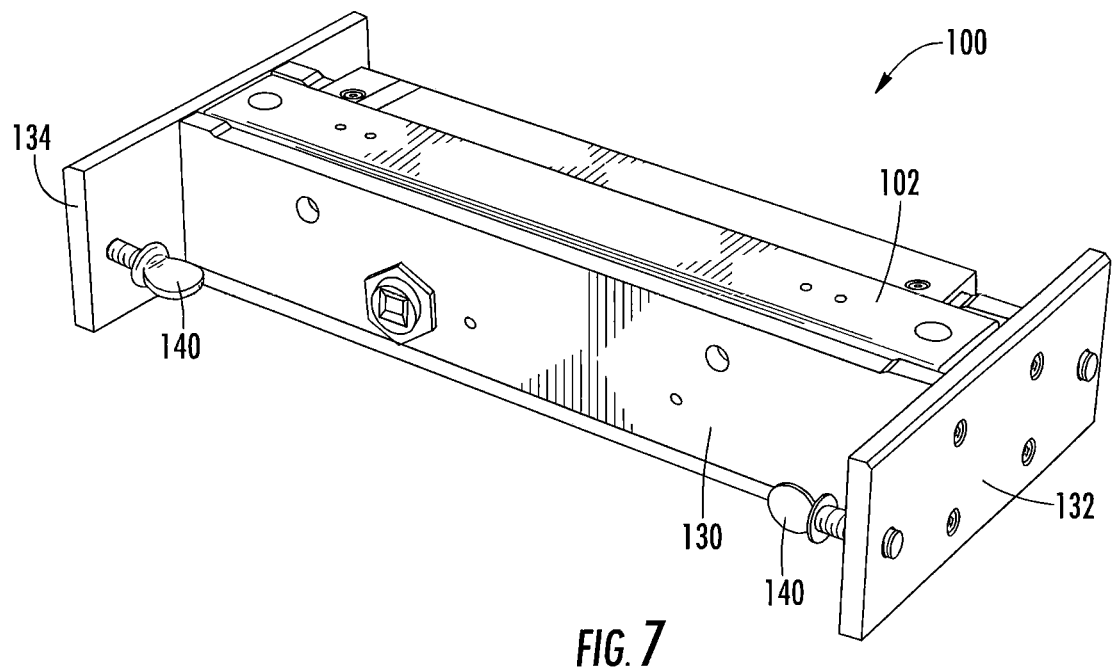
FIG. 7 is a perspective view of the system of FIG. 4 according to some embodiments.

FIG. 7 is a perspective view of the load and motion measurement system 100 according to some embodiments. The system 100 includes a housing 130. The housing 130 holds the loading platform 102 and, although not visible in FIG. 7, also holds the first and second load cells 104, 106 (FIG. 4). End plates 132, 134 may be at opposite ends of the housing 130.

Figure 8:
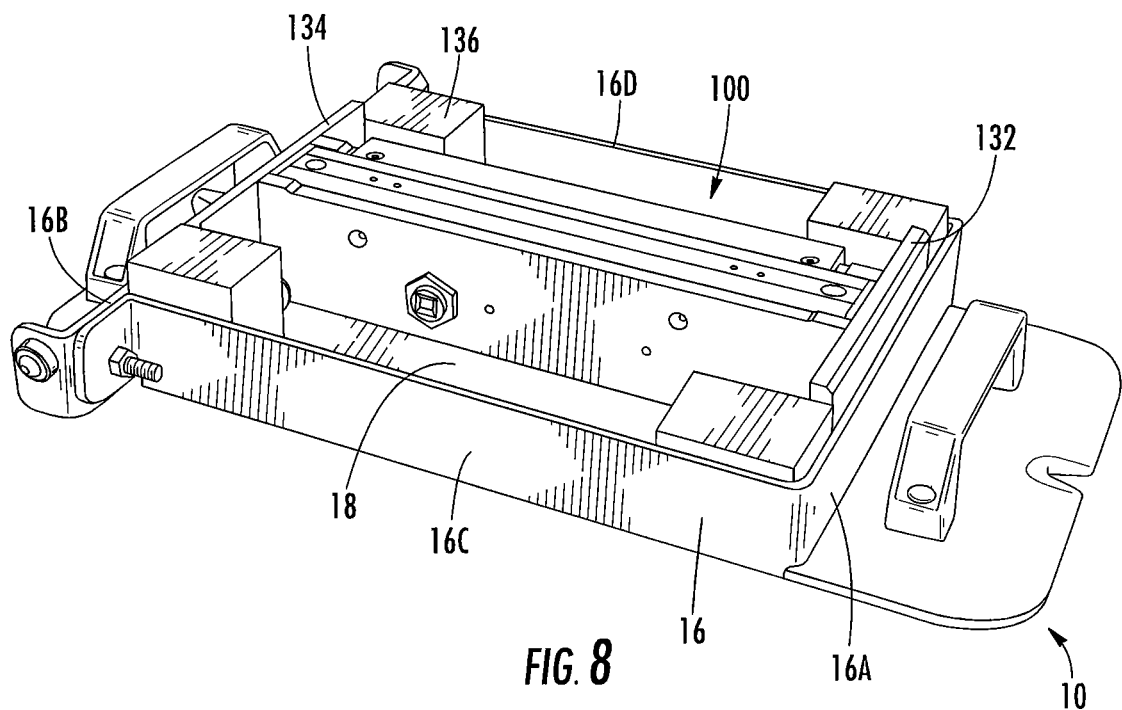
FIG. 8 is a perspective view of the system of FIG. 7 loaded in a sample tray for use in a Hamburg Wheel Tracker device.

FIG. 8 is a perspective view of the load and motion measurement system 100 held in a sample tray 10 that is the same or similar to the sample tray illustrated in FIG. 1 (with the samples 12 and the molds 14 removed from the sample tray). The system 100 is held within the sample compartment 16. More specifically, the sample compartment 16 may include first and second end walls 16A, 16B and first and second side walls 16C, 16D. The walls 16A, 16B, 16C, 16D may extend upwardly from a base 18 of the tray 10. The system 100 may be held in the sample compartment 16 with the first end plate 132 adjacent the first end wall 16A and the second end plate 134 adjacent the second end wall 16B. There are various wheel tracker manufacturers and each manufacturer may have a different sample tray. Spacer blocks 136 can allow the loading platform system 100 to be placed into the sample tray of the various wheel tracker manufacturers and are used to hold the system 100 in the correct position for that particular manufacturer. For example, the blocks 136 may be positioned between the end plates 132, 134 and the side walls 16C, 16D of the tray sample compartment 16.

Figure 9:
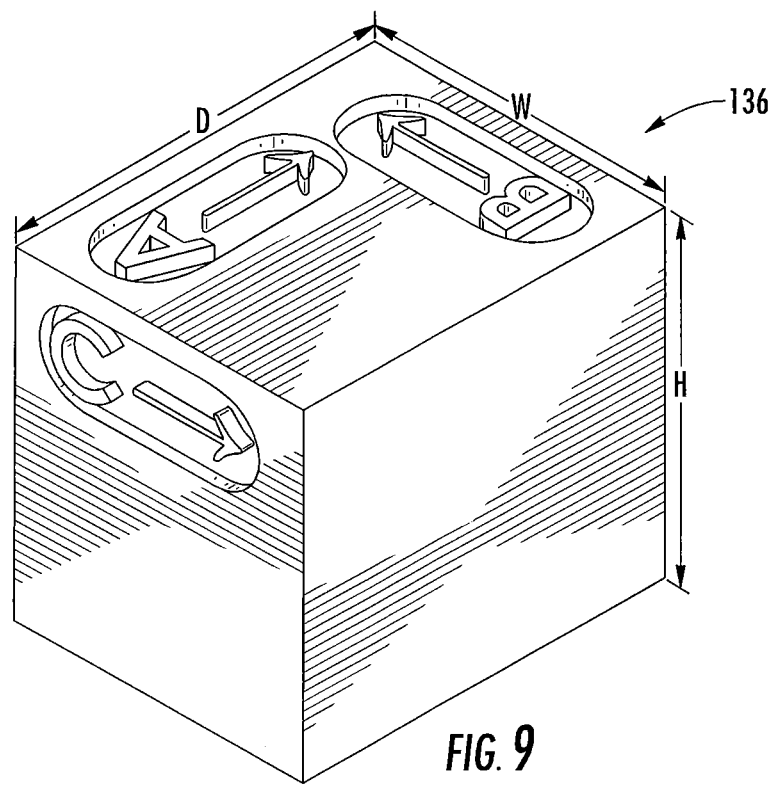
FIG. 9 is a perspective view of a sample block used to help hold the system in the sample tray of FIG. 8.

One of the spacer blocks 136 is shown in more detail in FIG. 9. The block 136 includes a height H, a width W, and a depth D. According to some embodiments, the height, the width W, and the depth D have different dimensions. For example, the height H may be greater than the width W and the depth D may be greater than the height H. Such a configuration allows the spacer blocks to be used to hold the load and motion measurement system 100 in three different types of sample trays each having different dimensions. The block 136 may include indicia such as the arrows and the labels "A," "B," and "C" to help the operator install the blocks in the proper orientation for a particular type of sample tray.

Figure 10:
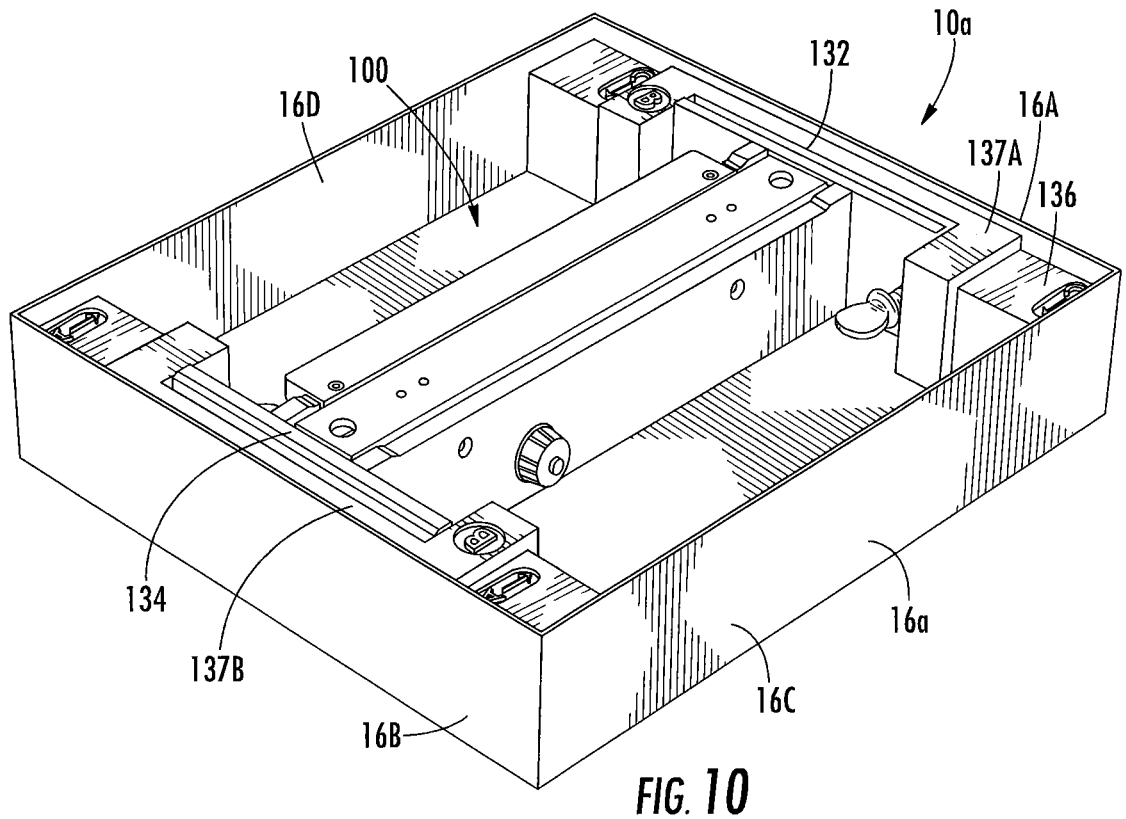
FIG. 10 is a perspective view of the system of FIG. 7 loaded in a sample tray for use in a Hamburg Wheel Tracker device that has different dimensions than the tray of FIG. 8.

This is illustrated in FIG. 8 and also in FIG. 10. In FIG. 10, the system 100 is positioned in the sample compartment 16a of a different type of sample tray 10a. Also shown in FIG. 10 are first and second end spacers 137A, 137B which may be used to accommodate the system 100 in the sample compartment 16a of the tray 10a that may have a length greater than the sample compartment 16 of the tray 10 shown in FIG. 8. As illustrated, the first end spacer 137A may be positioned between the first end plate 132 and the first end wall 16A of the tray compartment 16a and the second end spacer 137B may be positioned between the second end plate 134 and the second end wall 16B of the tray compartment 16a. One of the spacer blocks 136 may be positioned between the first side wall 16C of the sample compartment 16a and the first end spacer 137A, one of the spacer blocks 136 may be positioned between the second side wall 16D of the sample compartment 16a and the first end spacer 137A, one of the spacer blocks 136 may be positioned between the first side wall 16C of the sample compartment 16a and the second end spacer 137B, and one of the spacer blocks 136 may be positioned between the second side wall 16D of the sample compartment 16a and the second end spacer 137B.

Figure 11:
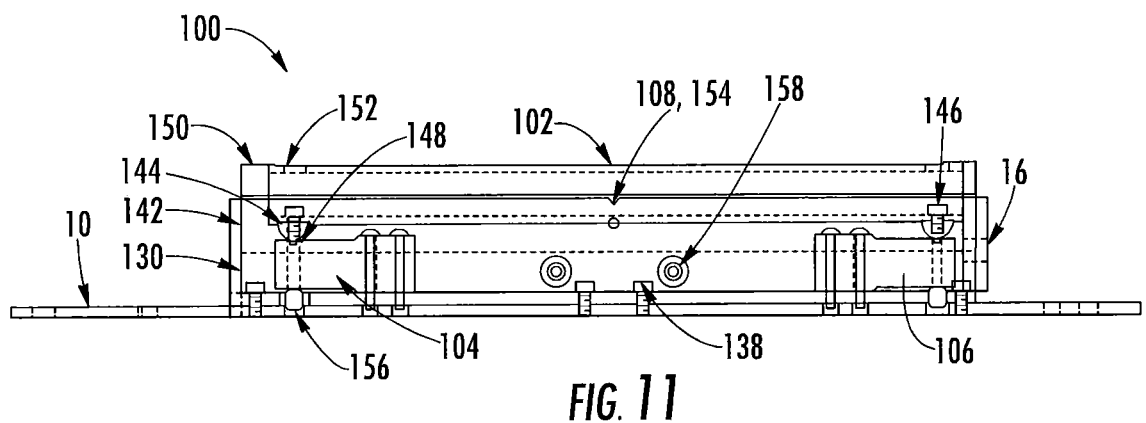
FIG. 11 is a side partial cutaway view illustrating additional details of the system of FIG. 4 according to some embodiments.

FIG. 11 is a side partial cutaway view of the loading platform system 100 held in the tray 10. The system 100 is placed and/or fastened into the manufacturer's specimen tray 10 in such a position that the center 108 of the system 100 is at the center point of the loading wheel path and tray sample compartment 16. Those skilled in the art will recognize that there are many ways to center the system 100 to the center of the specimen tray 10, either visually, using a straight edge to align possible centering marks on the system 100 to the center of the tray 10, using a string to do the same, or using a flexible steel rule to do the same, or other method easily recognized by those skilled in the art. The verification device may either be placed into the manufacturer's tray 10 or secured to the manufacturer's tray 10 using fasteners 138 or by other attachment features known to those skilled in the art. Additionally or alternatively, adjustment bolts or screws 140 may extend through the end plates 132, 134 and may be advanced to engage the ends walls 16A, 16B of the tray sample compartment 16 (FIGS. 7 and 8).

The system 100 may include the main housing 130, a wheel guide 142, and the loading platform 102. The loading platform 102 rests on load cells 104, 106 using, for example, interface members 144 such as half cylinders attached to the loading platform 102 with screws 146 at each end of the loading platform 102. It will be appreciated that other mechanisms known to those skilled in the art may be used to rest the loading platform 102 on the load cells 104, 106. Each half cylinder 144 may have a locating pin 148 thorough the center thereof that locates the loading platform 102 in the appropriate position on and between the load cells 104, 106 and keeps it positioned between the load cells 104, 106 but not significantly engage the load cells in a direction parallel to the motion of the wheel while the wheel is moving back and forth (see, for example, the wheel 54 in FIG. 3).

The wheel guide 142 has a plateau or platform 150 on both sides that starts the loading (or holds the wheel) initially above the loading platform 102. As the load (or wheel) moves, the wheel rolls down a ramp 152 between the plateau 150 and the loading platform 102 so that the load rests on the loading platform 102, e.g., between the locating pin 148 and the load point of load cell 106 and is weighed by load cells 104, 106.

The center 108 between load cells 104, 106 may be indicated by a notch 154 or the like in the manufacturers sample tray 10 that is centered between load cells 104, 106. Each load cell 104, 106 may be protected by a load cell stop 156 from excessive loads that may cause damage.

The electrical signals from the load cells 104, 106 may be transmitted to a connector or connector port 158 for connecting to one or more outside monitoring instruments (e.g., the data acquisition unit 110, the voltage source 112 and/or the computer or controller 114 shown in FIG. 5). It will be appreciated that the voltage source 112 may be contained in the main housing 130 and the connector port 158 may be connected wirelessly to and communicate wirelessly with the data acquisition unit 110 and/or the computer or controller 114.

When a load is placed on the loading platform 102 both load cells 104, 106 may register a load. The amount registered by each load cell 104, 106 depends on how far the load is from the load cell 104, 106. The sum of the load on each load cell 104, 106 will be equal to the load on the loading platform.

Figure 2:
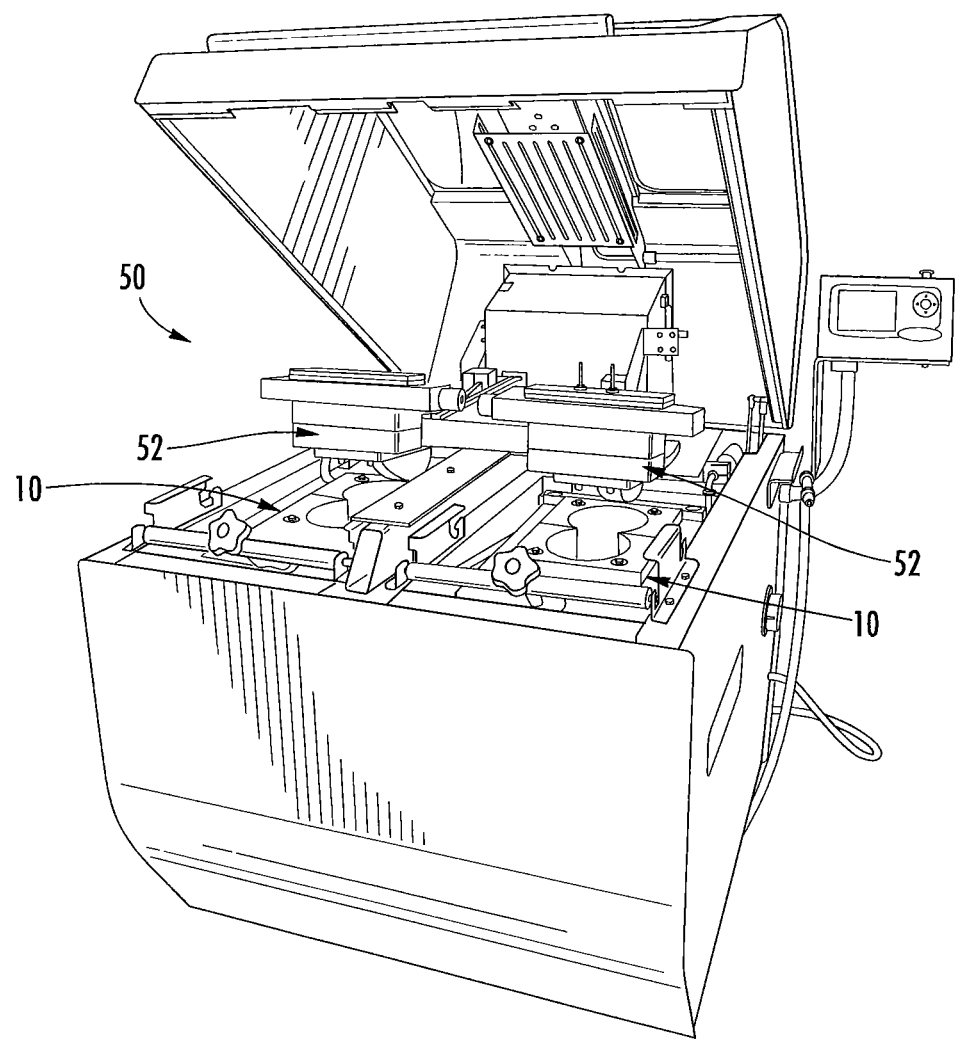
FIG. 2 is a perspective view of a Hamburg Wheel Tracker device.
Figure 3:
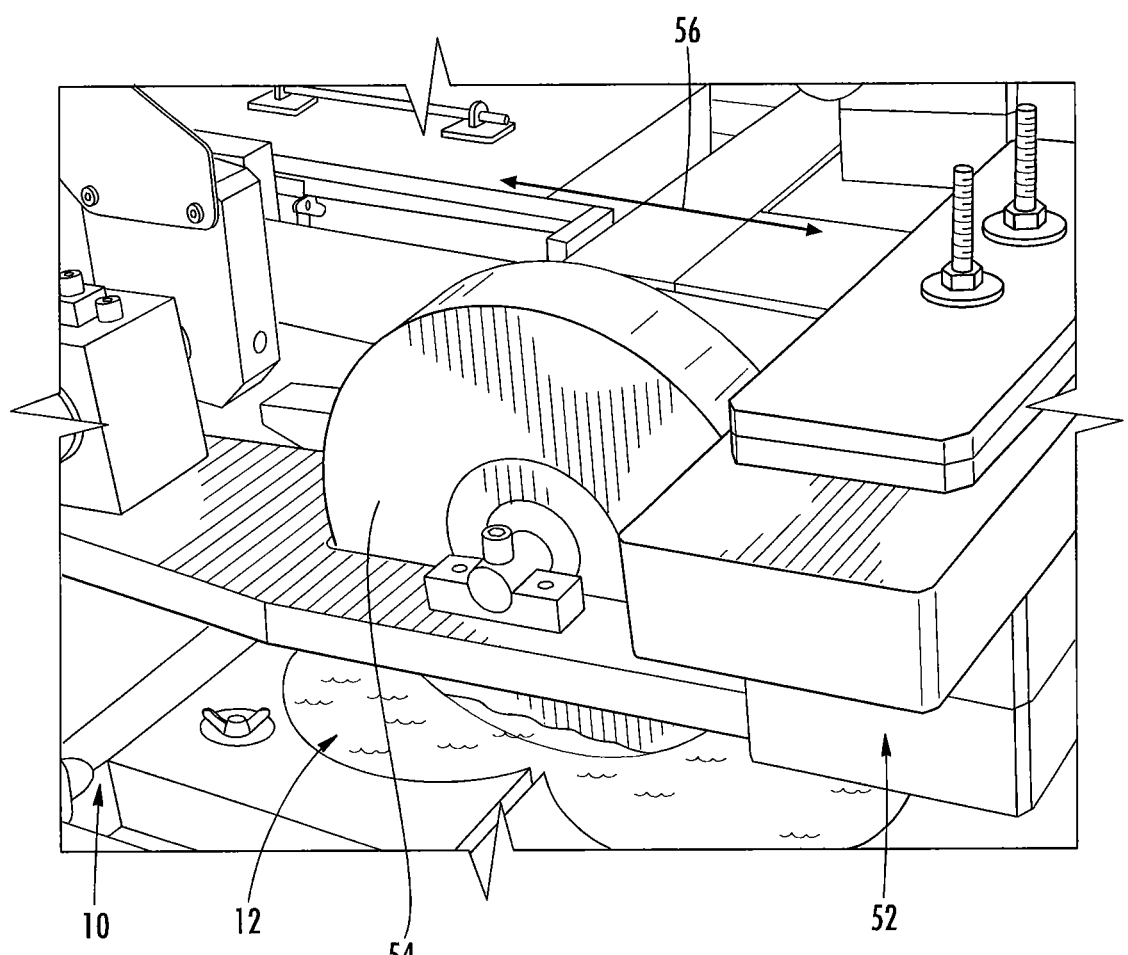
FIG. 3 is a fragmentary perspective view of the Hamburg Wheel Tracker device of FIG. 2.
Figure 12:
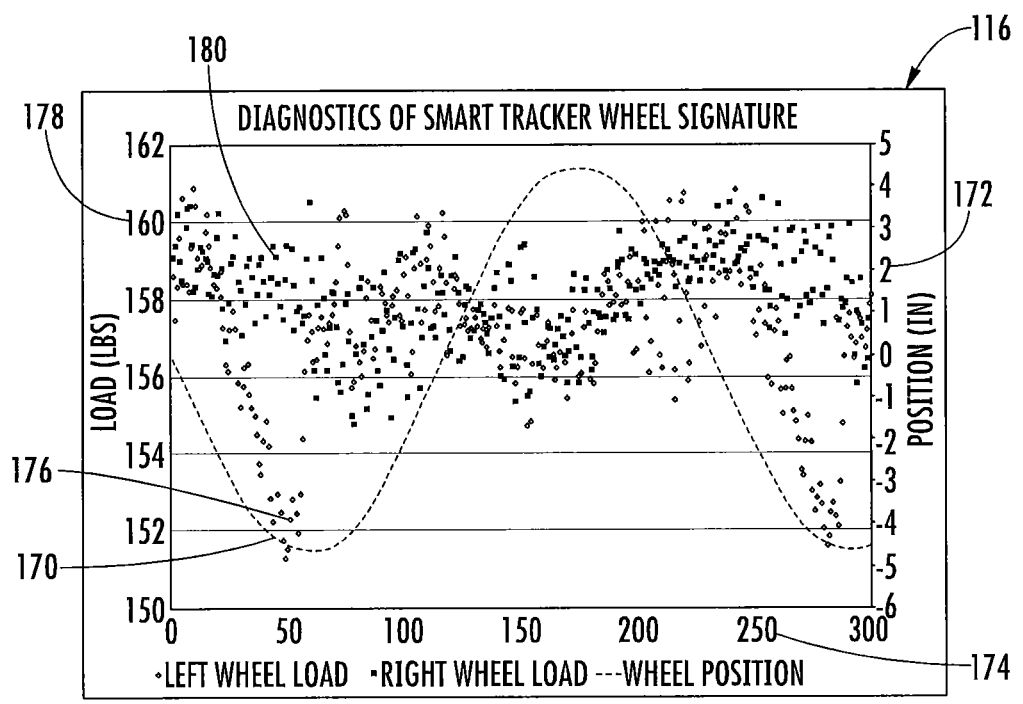
FIG. 12 is a screenshot illustrating diagnostics that can be performed on a Hamburg Wheel Tracker device by the system of FIG. 4.

FIG. 12 illustrates some diagnostics that can be carried out using the system 100 on a Hamburg Wheel Tracker device such as the device 50 shown in FIGS. 2 and 3. As illustrated, several plots may be displayed that depict the load of the wheel 54 as it moves across the platform as well as the position of the wheel. The data may be displayed on the controller or computer 114 shown in FIG. 5, for example. The plot 170 indicates the position of the wheel with respect to the center of motion. The position is indicated by the right axis 172 on the right hand side of the figure. Time is indicated by the bottom axis 174 and may be in units of milliseconds, seconds, or other time unit. Data 176 indicates the weight of the left wheel with load axis 178. It is important to note the large dip below 152 lbs that occurs for load data indicating that there may be a problem with the left wheel. This is compared to data 180 which shows load data from the right wheel and displays a much smaller variation. The steep dip in the load at this position indicates a mechanical problem with the wheel tracker. The system 100 is capable of performing diagnostics on the Hamburg Wheel Tracker device by studying the shape of the load data. Mechanical problems that may be electronically identified or diagnosed include, but are not limited to, pitting, eccentricity, non-parallelism and warping misalignment.

Figure 13:
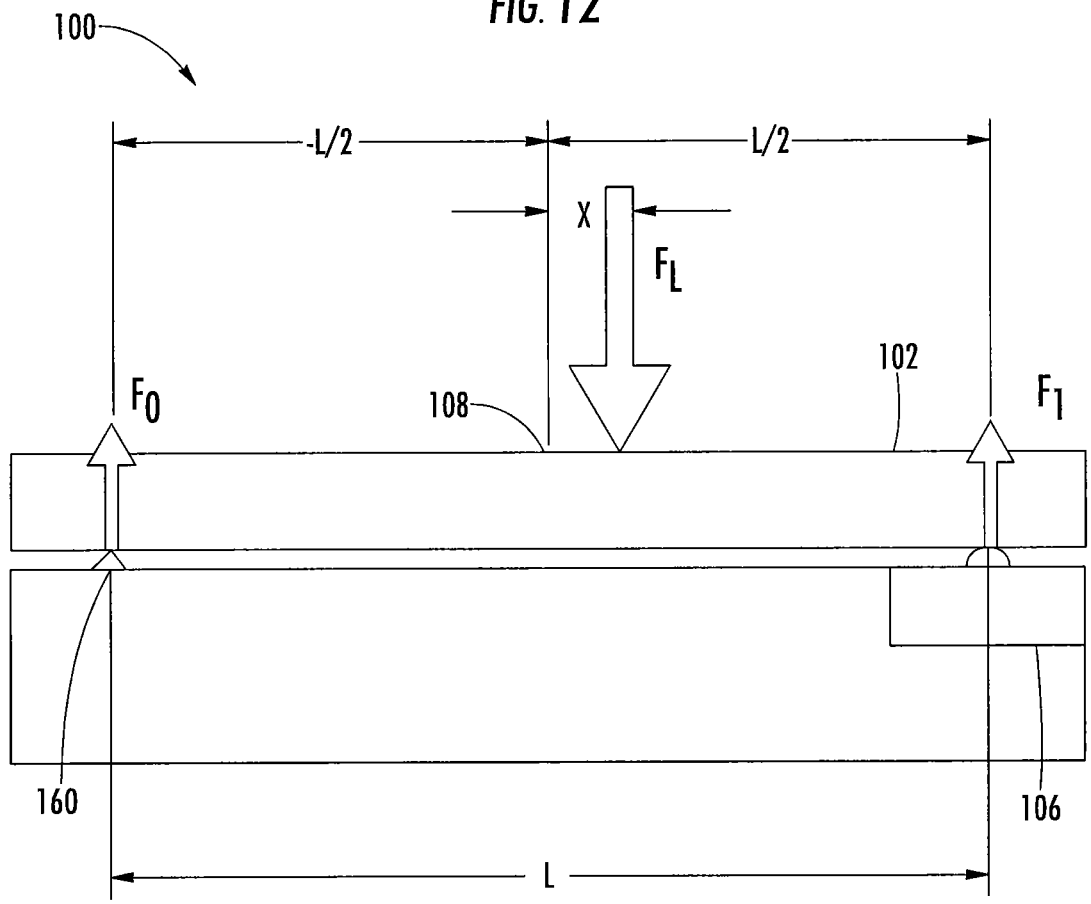
FIG. 13 schematically illustrates a load and motion measurement system including a load cell according to some other embodiments and the relationship between the forces on the load cell and the loading force.

FIG. 13 shows another embodiment of the system 100 capable of measuring the displacement using a single load cell. More specifically, FIG. 13 schematically illustrates of another embodiment of the system 100 for measuring load and displacement using a single load cell. The load $F_L$ is applied to the loading platform 102 between fulcrum 160 and the load cell 106. The load is applied at a position x just to the right of the midpoint 108 between the fulcrum 160 and the load cell 106. The load $F_L$ measured on the platform 102 will depend on the position of the load $F_L$ on the platform 102. The load may be measured directly on and above the load cell 106.

The position x from the center or midpoint 108 between the fulcrum 160 and the load cell 106 can be calculated by forming the ratio of the measured load on load cell 106 and the load $F_L$ multiplied by the length of travel L between the fulcrum 160 and the load cell 106. Subtracting from that half the length L allows a measurement of displacement from +L/2 to −L/2. This is shown in equation (3) below.

$$x = L\left(\frac{F_1}{F_L}\right) - \frac{L}{2} \qquad (3)$$

It can be seen that if the load is entirely situated on the fulcrum 160 then the load $F_1$ on load cell 106 is zero resulting in displacement of −L/2. Likewise, if the load $F_L$ is entirely situated on load cell 106 then the load F1 on load cell 106 is equal to the load $F_L$ and results in a displacement of +L/2. Those skilled in the art will recognize that the reference (or zero point) in equation 2 and 3 is the center of wheel translation, however, it may be the center, one end, or any other significant portion of the length.

Although the system 100 has been described as having one or two load cells, other arrangements are contemplated. For example, there may be three load cells, with the two load cells 104, 106 at ends of the loading platform 102 (FIG. 9) and with a third load cell at the midpoint between the load cells 104, 106. Other configurations are contemplated. For example, more than two load cells may be used such as placing a third load cell between the two load cells for an extended length, using four load cells where there are two pair on each end to provide enhanced stability, or other such geometries that may be envisioned for specific purposes.

Figure 14:
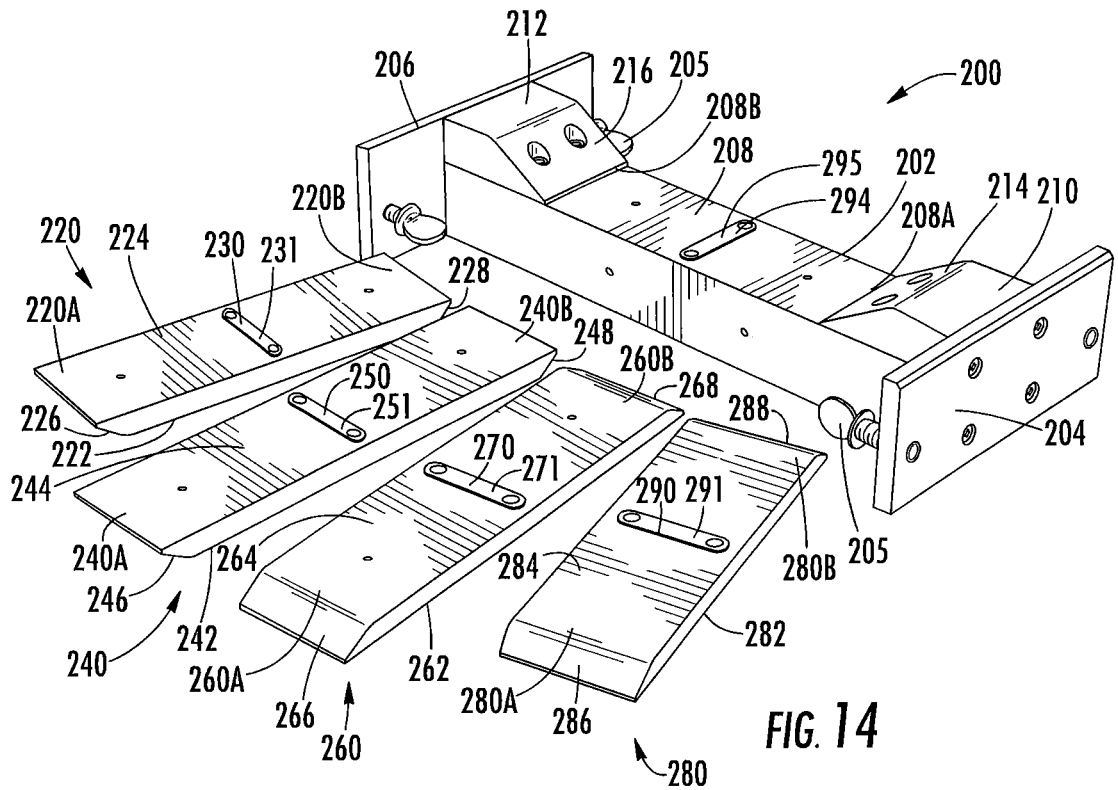
FIG. 14 is a perspective view of a vertical displacement measurement system according to some embodiments.
Figure 15:
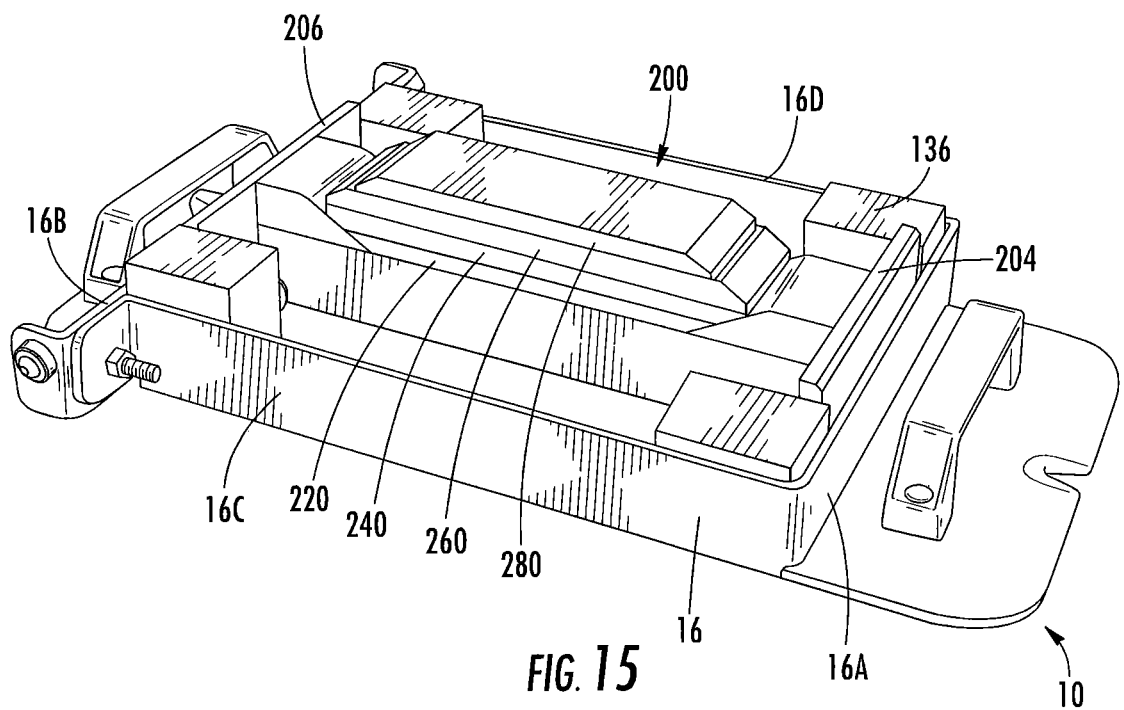
FIG. 15 is a perspective view of the system of FIG. 12 assembled and loaded in a sample tray for use in a Hamburg Wheel Tracker device.
Figure 16:
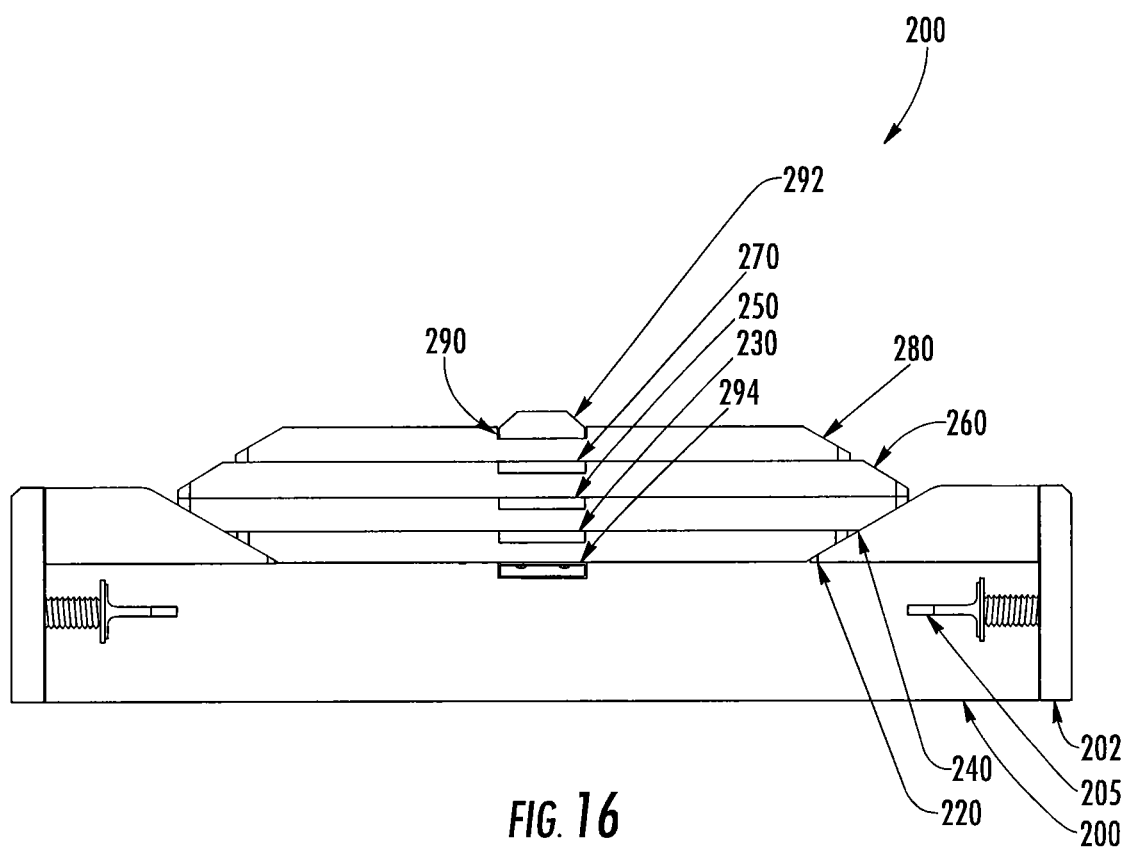
FIG. 16 is a side view of the vertical displacement measurement system of FIG. 14.

FIGS. 14-16 illustrate a vertical displacement measurement system 200 according to some embodiments. The system 200 is designed to raise the center of the wheel (e.g., the wheel 54 shown in FIG. 3) at specific vertical displacements which can then be compared to the vertical displacement measuring system on the Hamburg Wheel Tracker. In this embodiment the vertical displacement measurement system 200 is placed in the sample tray (FIG. 1) and in the same position as a sample would be placed in the test unit or Hamburg Wheel Tracker 50 (FIG. 2). In order to accommodate the sample trays of various manufacturers of wheel tracker machines, spacer blocks 136 may be used in different orientations for each specific manufacturer. The spacer blocks 136 may be the same as those described above in reference to FIG. 9.

More specifically, the system 200 includes a frame 202 and first and second end plates 204, 206 on opposite sides of the frame 202. The system 200 may be situated in the sample tray 10 with the first and second end plates 204, 206 adjacent the end walls 16A, 16B of the tray sample compartment 16. The system 200 may be secured using adjustment bolts or screws 205 that extend through the end plates 204, 206 and engage the end walls 16A, 16B. The spacer or support blocks 136 may be used to help hold the system 200 in position (e.g., between the end plates 204, 206 and the side walls 16C, 16D of the tray sample compartment 16).

The frame 202 may include a flat lower surface 208 and first and second flat upper surfaces 210, 212. A first ramp or inclined surface 214 may extend upwardly from a first end 208A of the lower flat surface 208 to the first upper flat surface 210. A second ramp or inclined surface 216 may extend upwardly from a second end 208B of the lower flat surface 208 to the second upper flat surface 212.

The system may include a plurality of height blocks or slats 220, 240, 260, 280. The first height block 220 may include a lower flat surface 222 and an upper flat surface 224. A first inclined end surface 226 may be at a first end 220A of the block 220 and a second inclined end surface 228 may be at a second end 220B of the block 220. Each of the first and second inclined end surfaces 226, 228 may extend from the lower flat surface 222 to the upper flat surface 224. A precision pad receiving feature 230 such as a groove may be on the upper flat surface 224.

The second height block 240 may include a lower flat surface 242 and an upper flat surface 244. A first inclined end surface 246 may be at a first end 240A of the block 240 and a second inclined end surface 248 may be at a second end 240B of the block 240. Each of the first and second inclined end surfaces 246, 248 may extend from the lower flat surface 242 to the upper flat surface 244. A precision pad receiving feature 250 such as a groove may be on the upper flat surface 244.

The third height block 260 may include a lower flat surface 262 and an upper flat surface 264. A first inclined end surface 266 may be at a first end 260A of the block 260 and a second inclined end surface 268 may be at a second end 260B of the block 260. Each of the first and second inclined end surfaces 266, 268 may extend from the lower flat surface 262 to the upper flat surface 264. A precision pad receiving feature 270 such as a groove may be on the upper flat surface 264.

The fourth height block 280 may include a lower flat surface 282 and an upper flat surface 284. A first inclined end surface 286 may be at a first end 280A of the block 280 and a second inclined end surface 288 may be at a second end 280B of the block 280. Each of the first and second inclined end surfaces 286, 288 may extend from the lower flat surface 282 to the upper flat surface 284. A precision pad receiving feature 290 such as a groove may be on the upper flat surface 284.

With reference to FIGS. 14-16, the height blocks 220, 240, 260, 280 may be positioned on the frame 202 in a stacked relationship. The lower surface 222 of the first block 220 may rest on the lower flat surface 208 of the frame 202. The first inclined end surface 226 of the block 220 may rest on (or be adjacent) the ramp 214 of the frame 202 and the second inclined end surface 228 of the block 220 may rest on (or be adjacent) the ramp 216 of the frame 202.

The lower surface 242 of the second block 240 may rest on the upper surface 224 of the first block 220. The first inclined end surface 246 of the block 240 may rest on (or be adjacent) the ramp 214 of the frame 202 and the second inclined end surface 248 of the block 240 may rest on (or be adjacent) the ramp 216 of the frame 202.

The lower surface 262 of the third block 260 may rest on the upper surface 244 of the second block 240. The first inclined end surface 266 of the block 260 and the first upper flat surface 210 of the frame 202 may define an obtuse angle therebetween. Likewise, the second inclined end surface 268 of the block 260 and the second upper flat surface 212 of the frame 202 may define an obtuse angle therebetween.

The lower surface 282 of the fourth block 280 may rest on the upper surface 264 of the third block 260. The first inclined end surface 286 of the block 280 and the first upper flat surface 210 of the frame 202 may define an obtuse angle therebetween. Likewise, the second inclined end surface 288 of the block 280 and the second upper flat surface 212 of the frame 202 may define an obtuse angle therebetween.

The first inclined end surfaces 266, 286 of the blocks 260, 280 may be generally coplanar. The first inclined end surfaces 266, 286 of the blocks 260, 280 may define a ramp from the first upper flat surface 210 of the frame 202 to the upper surface 284 of the block 280. When the block 280 is removed from the stack, the first inclined end surface 266 of the block 260 may define a ramp from the first upper flat surface 210 of the frame 202 to the upper surface 264 of the block 260.

It will be appreciated that the wheel of the Hamburg Wheel Tracker device may only be loaded on the stack of blocks in one direction (e.g., from the first upper flat surface 210 of the frame onto the stack of blocks). Therefore, the second upper flat surface 212 and/or the second ramp 216 of the frame and/or the block second inclined surfaces 228, 248, 268, 288 may not be used in some embodiments. However, these features may be desirable such that the blocks can be reversible and/or symmetrical, for example.

In use, all height blocks 220, 240, 260, 280 may initially be on the frame 202. The wheel (e.g., the wheel 54 shown in FIG. 3) is then moved horizontally and rolls up the incline to the highest point which may be a precision pad 292 that is received in the groove 290 on height block 280. Once this displacement is recorded, the wheel may be retracted and the precision pad 292 may be removed leaving behind height block 280. Once this displacement is recorded the wheel is again retracted and height block 280 may be removed from the stack. Precision pad 292 may be placed on top of groove 270 which is defined in height block 260. The wheel may again be brought forward and move up the incline and rest on precision pad 292 on height block 260. This process is continued for grooves 270, 250, 230 on blocks 260, 240, and 220, respectively. When enough of the vertical displacement blocks are removed, the wheel rolls down the frame 202 utilizing the ramp 214. To obtain vertical displacement verification with the wheel going up, the process described above may be reversed. While the above embodiment utilizes four height blocks, those skilled in the art will readily recognize that the use of more than four height blocks may also be used to accomplish essentially the same results.

Embodiments can be configured to have standard certified gauge blocks wherein the height blocks 220, 240, 260, and 280, are designed to accept and mechanically constrain the certified gauge blocks from movement as the load is applied. As height blocks 220, 240, 260, and 280 are added the certified gauge blocks are kept aligned and on top of each other through the constraining action of height blocks 220, 240, 260, and 280. The standard certified gauge blocks are also designed so that the standard certified gauge blocks protrude slightly above the constraining height blocks.

An example of this configuration is illustrated in FIGS. 17-20. The system may additionally include a height block or slat 300 that rests on the height block 280. The height block 300 may include a lower surface 302, an upper surface 304 and first and second opposite inclined end surfaces 306, 308 that each extend between the lower surface 302 and the upper surface 304.

Figure 17:
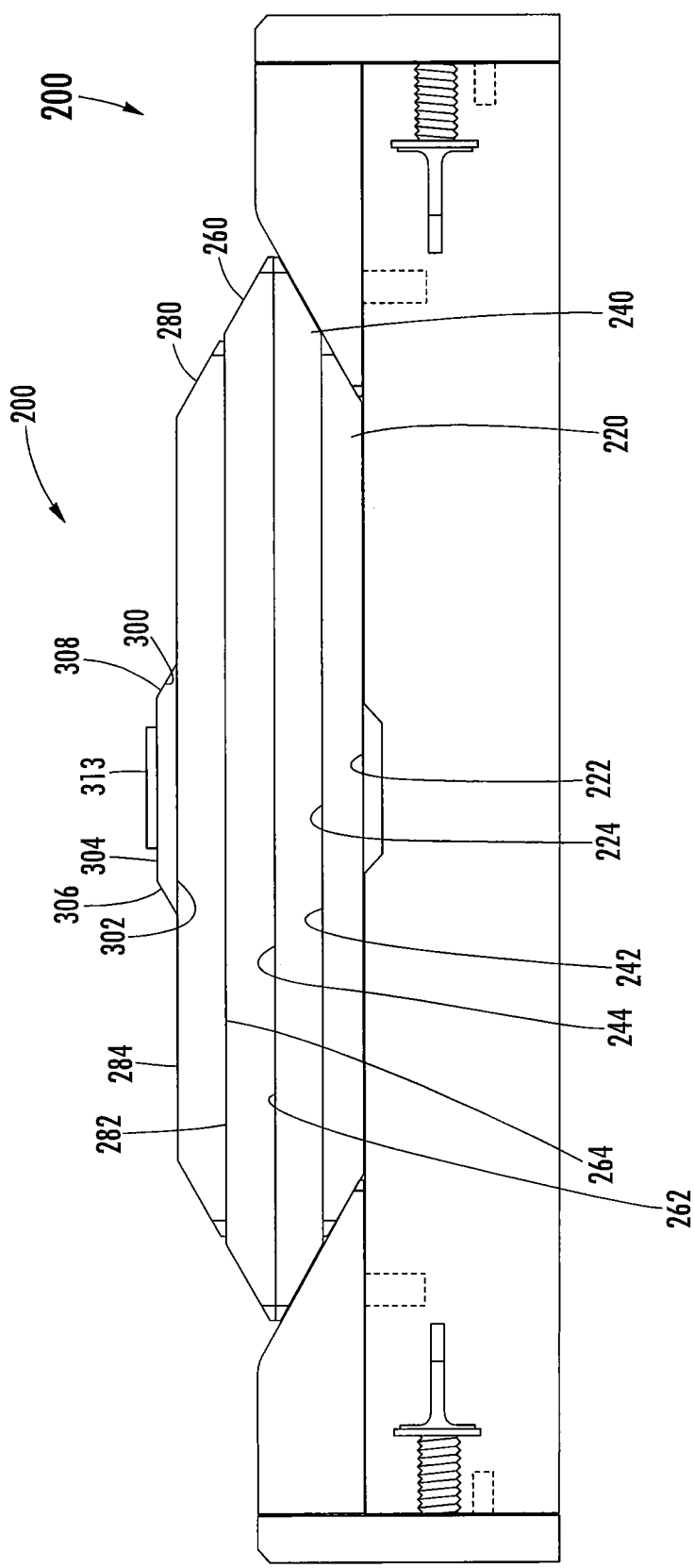
FIG. 17 is a side view of a vertical displacement measurement system according to some other embodiments.
Figure 18:
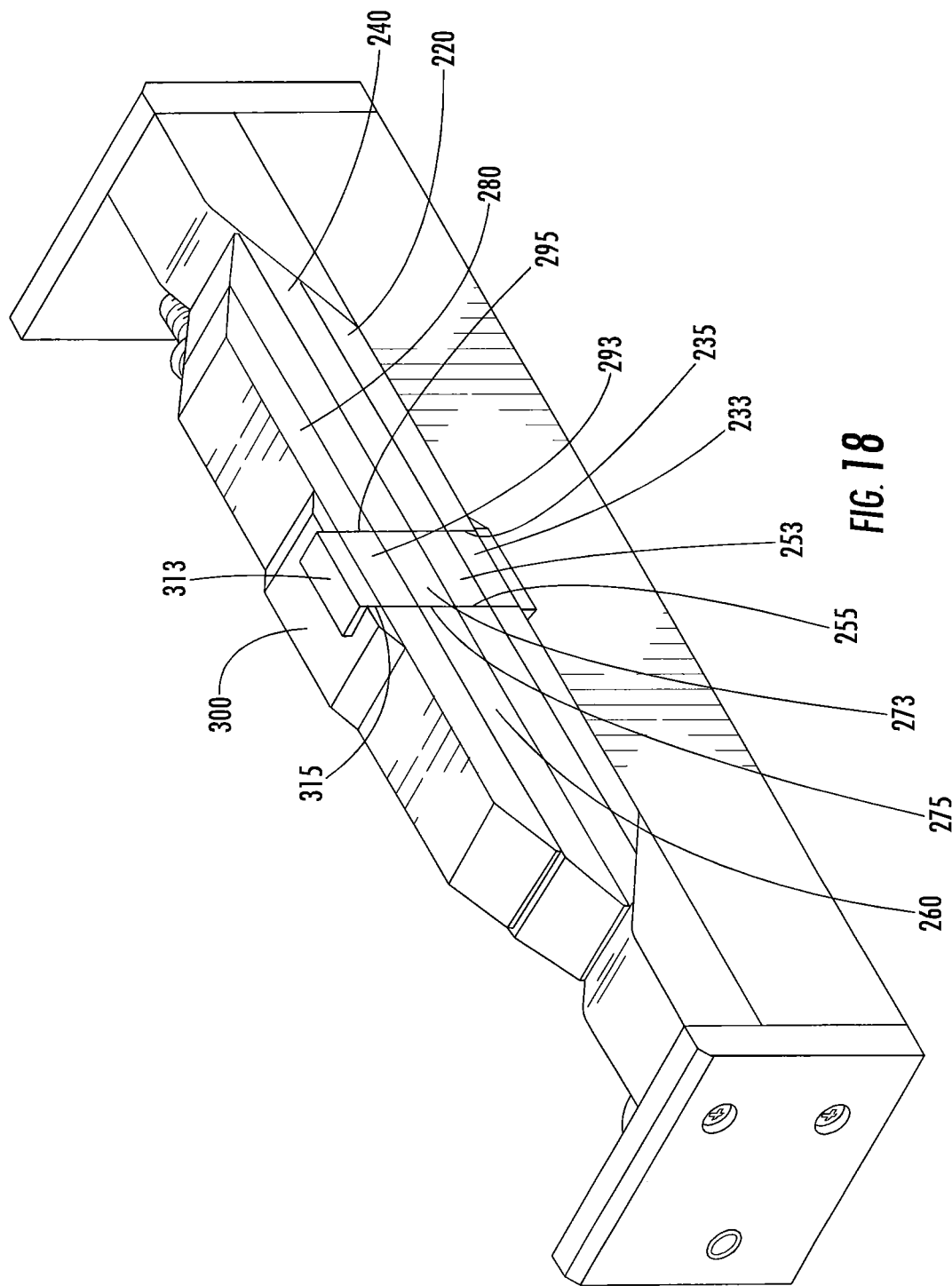
FIG. 18 is a perspective longitudinal sectional view of the system of FIG. 17.
Figure 19:
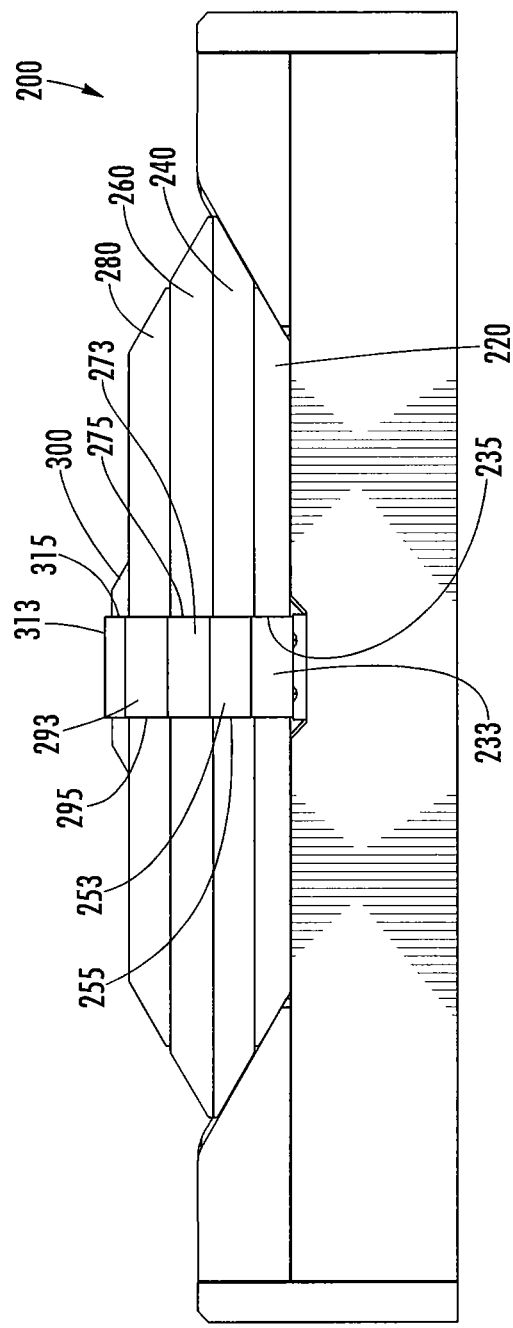
FIG. 19 is a side longitudinal sectional view of the system of FIG. 17.

Referring to FIGS. 17-19, an aperture 315 may be defined in the height block 300 and may extend between the lower and upper surfaces 302, 304 thereof, an aperture 295 may be defined in the height block 280 and may extend between the lower and upper surfaces 282, 284 thereof, an aperture 275 may be defined in the height block 260 and may extend between the lower and upper surfaces 262, 264 thereof, an aperture 255 may be defined in the height block 240 and may extend between the lower and upper surfaces 242, 244 thereof, and an aperture 235 may be defined in the height block 220 and may extend between the lower and upper surfaces 222, 224 thereof.

A gauge block 313 may be held in the aperture 315 and may extend above the upper surface 304 of the height block 300. A gauge block 293 may be held in the aperture 295 and/or the aperture 315 and may extend above the upper surface 284 of the height block 280. A gauge block 273 may be held in the aperture 275 and/or the aperture 295 and may extend above the upper surface 264 of the height block 260. A gauge block 253 may be held in the aperture 255 and/or the aperture 275 and may extend above the upper surface 244 of the height block 240. A gauge block 233 may be held in the aperture 235 and/or the aperture 255 and may extend above the upper surface 224 of the height block 220.

Figure 20:
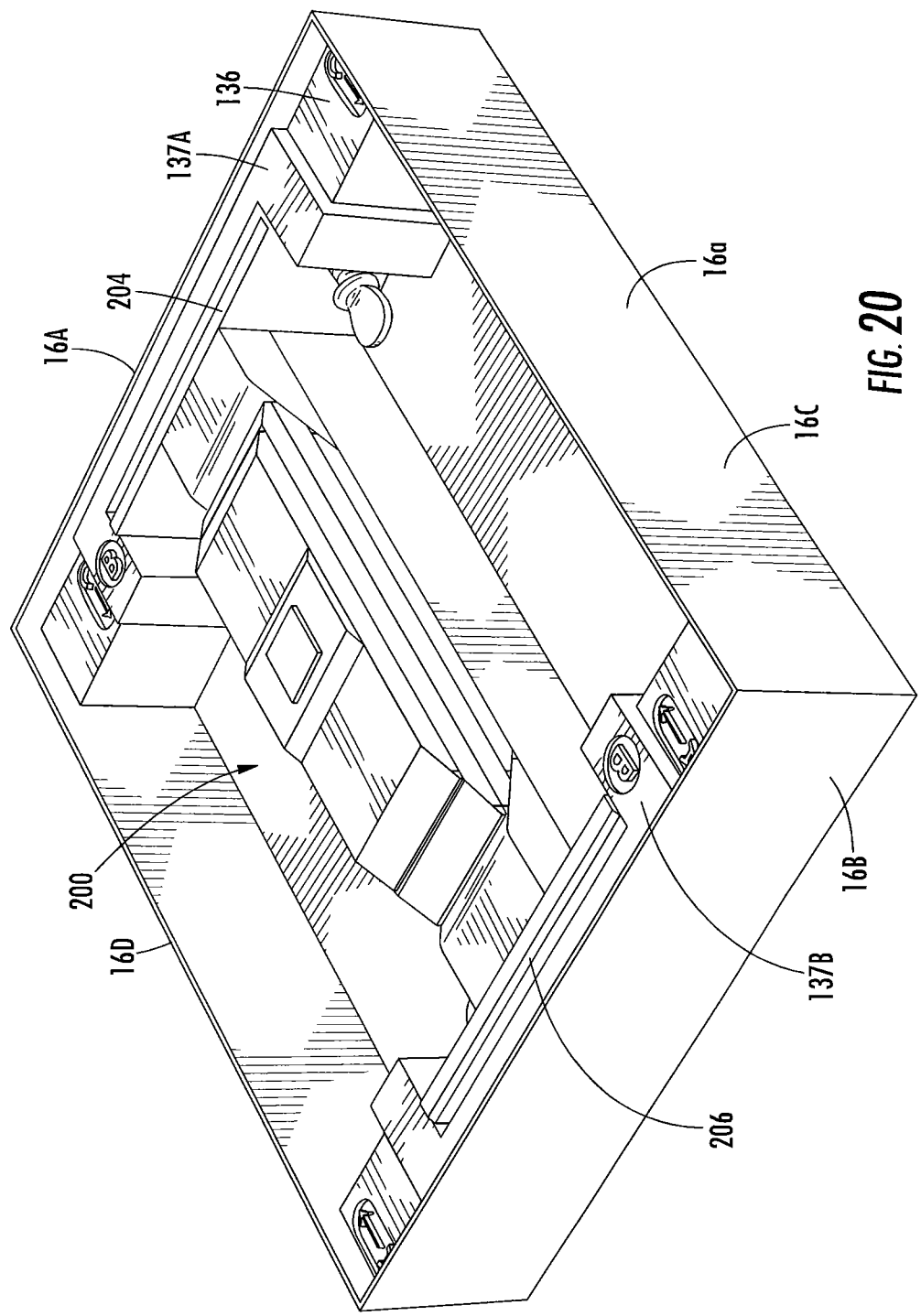
FIG. 20 is a perspective view of the system of FIG. 17 loaded in a sample tray for use in a Hamburg Wheel Tracker device that has different dimensions than the tray of FIG. 15.

In FIG. 20, the system 200 of FIGS. 17-19 is positioned in the sample compartment 16a of a different type of sample tray 10a. Also shown in FIG. 20 are the first and second end spacers 137A, 137B which may be used to accommodate the system 200 in the sample compartment 16a of the tray 10a that may have a length greater than the sample compartment 16 of the tray 10 shown in FIG. 15. As illustrated, the first end spacer 137A may be positioned between the first end plate 204 and the first end wall 16A of the tray compartment 16a and the second end spacer 137B may be positioned between the second end plate 206 and the second end wall 16B of the tray compartment 16a. One of the spacer blocks 136 may be positioned between the first side wall 16C of the sample compartment 16a and the first end spacer 137A, one of the spacer blocks 136 may be positioned between the second side wall 16D of the sample compartment 16a and the first end spacer 137A, one of the spacer blocks 136 may be positioned between the first side wall 16C of the sample compartment 16a and the second end spacer 137B, and one of the spacer blocks 136 may be positioned between the second side wall 16D of the sample compartment 16a and the second end spacer 137B.

Figure 21:
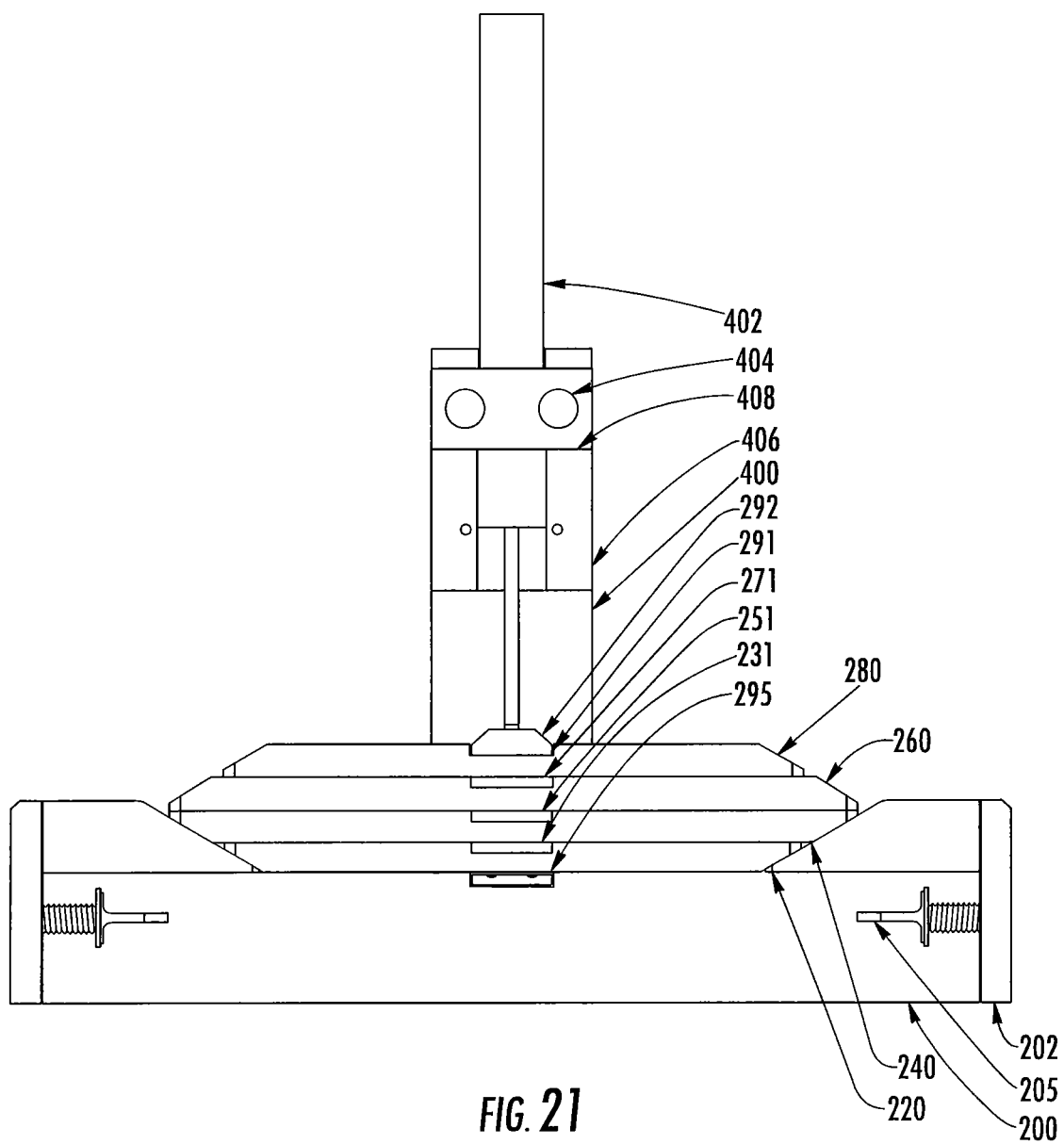
FIG. 21 is a side view of the vertical displacement measurement system of FIG. 12 used to verify the accuracy of a vertical displacement transducer.

FIG. 21 shows the vertical displacement measurement system 200 with attachable vertical linear variable displacement transducer holding mechanism 400 (holding mechanism), where any transducer accomplishing the same result will be referred to as an LDT or LVDT. The holding mechanism 400 may be used to verify the vertical displacement measured by an LDT. The LDT 402 is fixed to the vertical displacement measuring apparatus using the attachable LDT holding mechanism 400. The LDT 402 is fastened and made immobile using the fastening system 404, 406, 408. The LDT 402 is situated directly above the vertical displacement measurement system 200 with the measuring point in contact with the precision pad 292 (or the gauge block 313 shown in FIGS. 17-19). Specifically, the LDT 402 is moved to such a position that the probe is able to sense a change upon the removal of the precision pad 292 (or the gauge block 313) and subsequent removals of height blocks 280, 260, 240 and 220. In addition, the LDT 402 is so arranged that it can be made to directly contact precision height pads 291, 271, 251, 231 and 295 (or gauge blocks 313, 293, 273, 253, 233) on height blocks 300, 280, 260, 240, 220 and on the frame lower flat surface 208, respectively (see also FIG. 14). When the first precision height pad 292 is removed, the LDT 402 extends to a new known position which is compared with the measured position. Then, height block 280 is removed and precision pad 292 may be placed in or on groove 270 (FIG. 13) and the LDT 402 may extend to a new position against the precision height pad 292 of known height, which may be compared with the LDT reading. This is continued by removing or replacing height block assemblies as necessary. Once all height block assemblies have been removed the process may be reversed to verify the LDT 402 in the opposite direction.

Figure 22:
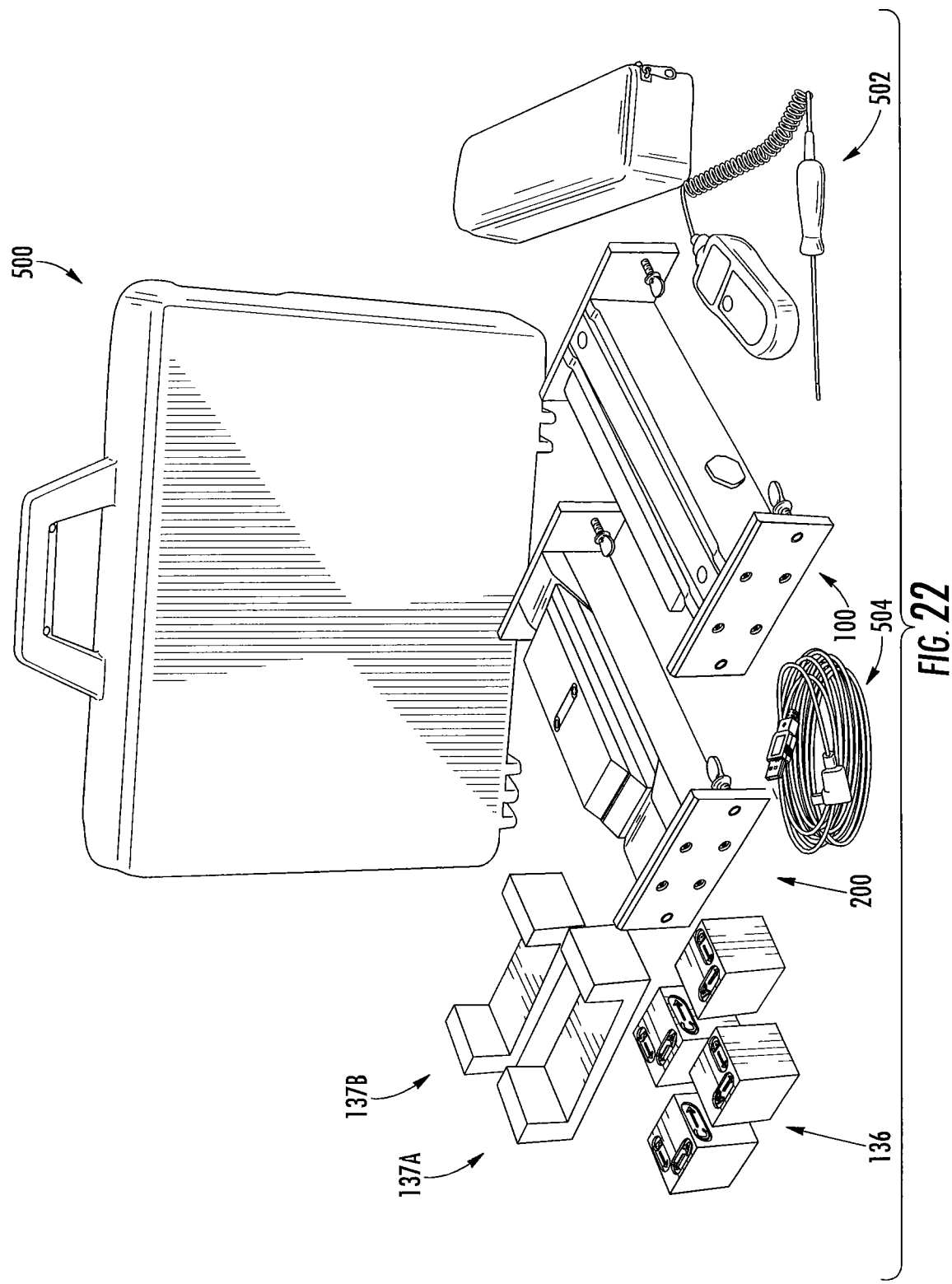
FIG. 22 is a perspective view of a kit for calibrating and/or verifying the proper operation of a Hamburg Wheel Tracking device according to some embodiments.

FIG. 22 illustrates a kit 500 for calibrating and/or verifying the proper operation of a Hamburg Wheel Tracking device according to some embodiments. The kit 500 may include the load and motion measurement system 100, the vertical displacement measurement system 200, and/or a temperature probe 502. The temperature probe 502 may be used to measure and verify the temperature of the water in which samples are held in the Hamburg Wheel Tracker device. The kit may further include a cord 504 (e.g., a USB cord) for connecting the load and motion measurement system 100 (e.g., at the port 158 in FIG. 11) and a computer (e.g., the computer 114 in FIG. 5) acting as the controller for outputting the operational parameters associated with a wheel of the Hamburg Wheel Tracking device. The cord 504 may also provide power to the load and motion measurement system 100. The kit 500 may also include an alignment bar to mark the center of the tray 10 to ensure the center of the load and motion measurement system is centered with specimen location. The alignment bar can be a bar of known thickness or length used to measure the location of the center of the tray. It accounts for the thickness of the molds and the allowable space or gap between the molds 14 due to cutting samples 16 to properly center the load and motion measurement system. The kit 500 may further include the spacer blocks 136 and/or the end spacers 137A, 137B. In some embodiments, the kit 500 includes the vertical displacement transducer holding mechanism 400 and/or the LDT or LVDT 402 (FIG. 21). The LDT or LVDT may be calibrated and attached to a jig that can be set at different heights and the machine LVDT can be checked against the provided LVDT.

The systems proposed in this application can have four different measurement capabilities: a load measurement system, a vertical displacement verification system, a temperature measurement system, and a motion measurement system that captures the wheel motion waveform shape, the speed at the center of the wheel motion, the center of motion, the period of wheel motion, and the amplitude of the wheel motion waveform. The wheel load is measured using one or more load cells and the system is capable of measuring the load at any position along the line of the movement. The vertical displacement is verified using a system of blocks and/or spacers for measuring displacements either under the wheel or utilizing these blocks and/or spacers to verify the linear displacement measuring system independently. The HWT system is able to measure the rut depth within 0.15 mm over a 20 mm span (per AASHTO T324). The temperature is verified using a calibrated temperature device. The displacement along the wheel path is measured using the difference in load cell measurements when the load is supported between the two load cells. This displacement measurement is used in conjunction with a timing element to obtain the shape, speed at center, and period of the load applied to the sample.

Currently, separate methods and devices are employed to verify the parameters used by the dynamic operation of the HWT. To verify that the horizontal displacement of the loading mechanism is correct requires a physical measurement of the horizontal load displacement using a ruler of some nature. This can consist of using a scaled ruler to mark the position of the wheel. Given that the time of one wheel pass is approximately one second to travel 9 inches (230 mm), video methods have been used to measure the horizontal displacement versus time characteristics of the loading. Current video methods use frame rates up to 200 frames per second to capture the motion. Using a reference point on the moving object and a scale appropriate to the video, the position of the wheel in each frame can be manually extracted to obtain the displacement versus time behavior. This process is time consuming, tedious, and prone to human error. The benefit of this process is a time versus displacement history allows the extraction of information about the wheel speed at the center of the wheel path, the length of the wheel path, and the waveform pattern of the wheel movement along the wheel path. With the systems described herein, the data acquisition and post-processing can be completed without human intervention within 30 seconds to two minutes, typically about 60 seconds, to obtain this information.

Verifying the load usually occurs by physically placing a load cell beneath the loading mechanism in a static arrangement. One drawback of this method is state of the practice load cells usually have low accuracy in the verification range, which increases the uncertainty of the measurement, and are difficult to position consistently, which affects the reproducibility of the load measurement. Another weakness is the load is verified in only one spot, the center of the motion. Again another weakness is that of having one's hand under a 158 lb steel load presenting a potential risk of injury. The other positions are assumed to have the same load which assumption is not guaranteed. Finally, these measurements are static measurements rather than moving or dynamic measurements even though the test is performed with a dynamic wheel load. The systems described herein can solve these problems by measuring the dynamic load along the whole wheel path with high accuracy load cells using beam theory.

Current systems for verifying the vertical displacement measurement consist of measuring the height of the loading wheel when gauge blocks are placed under the wheel, or removing the measuring linear displacement transducer and using a micrometer or gauge blocks to verify the transducer outside the wheel tracker. When using gauge blocks, the wheel must be lifted and the block placed carefully underneath; then, the wheel is slowly lowered onto the block. This presents a risk of injury since the gauge block is usually small and the weight of the wheel is significant. The embodiments described herein provide methods and systems for the machine to drive the wheel up onto the blocks to prevent users from lifting the wheel and inserting blocks under the wheel so as to produce significant risk of injury.

In summary, the verification systems described herein are a major improvement over the separate measurements mentioned above. This instrument may be in a single package that performs all the measurements described above. This instrument can measure at one time: dynamic load, displacement from center of motion, center of motion, waveform shape of displacement, and speed at the center of motion or any other point along which the motion occurs. There is no response time delay in the measurements as there is using video capture; the displacement data is virtually instantaneous. The device includes a method to verify the linear displacement transducer that measures the rut depth as well as a temperature measurement system to verify the temperature for specimen conditioning. All of these measurements are achieved with a device that reduces the operator error, quickly analyzes the data to provide a pass/fail result, and increases the safety for the operator.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed is:

1. A kit for calibrating and verifying the proper operation of a Hamburg Wheel Tracking device, the kit comprising:
    a load and motion measurement system comprising:
        a housing;
        at least one load cell held in or by the housing;
        a load platform held in or by the housing and resting on the at least one load cell; and
        a controller operatively associated with the at least one load cell;
        wherein the load and motion measurement system is configured to be received in a sample tray that is held in the Hamburg Wheel Tracker device;
        wherein the controller is configured to determine operational parameters associated with a wheel of the Hamburg Wheel Tracking device that rolls along the load platform; and
    a vertical displacement measurement calibration and verification system comprising:
        a frame;
        a plurality of height blocks configured to be selectively stacked on the frame;
        wherein the frame is configured to be received in a sample tray that is held in the Hamburg Wheel Tracker device such that a wheel thereof rolls onto the frame and/or one or more of the height blocks stacked thereon to verify the accuracy of a vertical displacement device associated with the Hamburg Wheel Tracker device.

2. The kit of claim 1 wherein the operational parameters comprise at least one of dynamic wheel load, wheel position over time, wheel speed, and a wheel waveform.

3. The kit of claim 1 further comprising a temperature probe for measuring a water temperature of water in a water bath in which the sample tray is configured to be held in the Hamburg Wheel Tracker device.

4. The kit of claim 1 further comprising a cord for connecting the load and motion measurement system to a computer acting as the controller for outputting the operational parameters associated with a wheel of the Hamburg Wheel Tracking device.

5. The kit of claim 1 further comprising a plurality of spacer blocks, each spacer block having a height, width and depth, wherein the spacer blocks are configured to be positioned in a sample compartment of a first sample tray in a first orientation with the spacer blocks between the load and motion measurement system and/or the vertical displacement measurement calibration and verification system and a wall of the sample compartment, wherein the spacer blocks are configured to be positioned in a sample compartment of a second sample tray having dimensions different than the first sample tray in a second orientation with the spacer blocks between the load and motion measurement system and/or the vertical displacement measurement calibration and verification system and a wall of the sample compartment, and wherein the spacer blocks are configured to be positioned in a sample compartment of a third sample tray having dimensions different than the first and second sample trays in a third orientation with the spacer blocks between the load and motion measurement system and/or the vertical displacement measurement calibration and verification system and a wall of the sample compartment.

6. A load and motion measurement system for use with a Hamburg Wheel Tracker device, the system comprising:
   a housing;
   at least one load cell held in or by the housing;
   a load platform held in or by the housing and resting on the at least one load cell; and
   a controller operatively associated with the at least one load cell;
   wherein the load and motion measurement system is configured to be received in a sample tray that is held in the Hamburg Wheel Tracker device;
   wherein the controller is configured to determine operational parameters associated with a wheel of the Hamburg Wheel Tracking device that rolls along the load platform.

7. The system of claim 6 wherein the at least one load cell comprises a first load cell and a second load cell that is spaced apart from the first load cell.

8. The system of claim 7 wherein the first load cell is at a first end portion of the housing and a second load cell at a second opposite end portion of the housing.

9. The system of claim 6 further comprising a first end plate at a first end portion of the housing and a second end plate at a second opposite end portion of the housing, wherein the load and motion measurement system is configured to be received in a sample compartment of the sample tray with the first end plate adjacent a first end wall of the sample compartment and the second end wall adjacent a second end wall of the sample compartment.

10. The system of claim 9 further comprising:
    at least one first adjustment mechanism that is extendable through the first end plate and is configured to be advanced through the first end plate to engage the first end wall of the sample compartment; and
    at least one second adjustment mechanism that is extendable through the second end plate and is configured to be advanced through the second end plate to engage the second end wall of the sample compartment.

11. The system of claim 10 wherein the operational parameters comprise at least one of dynamic wheel load, wheel position over time, wheel speed, and a wheel waveform.

12. The system of claim 11 wherein the controller is configured to compare the wheel waveform with a theoretical waveform.

13. The system of claim 6 further comprising a display, wherein the controller is configured to direct the display to display the operational parameters.

14. The system of claim 6 further comprising a connection port in or on the housing that is configured to receive a cord to connect to the controller.

15. The system of claim 6 wherein the at least one load cell and/or at least one electronic component associated therewith is configured to wirelessly communicate with the controller.

16. A vertical displacement measurement calibration and verification system for use with a Hamburg Wheel Tracker device, the system comprising:
    a frame;
    a plurality of height blocks configured to be stacked on the frame;
    wherein the frame is configured to be received in a sample tray that is held in the Hamburg Wheel Tracker device such that a wheel thereof rolls onto the frame and/or one or more of the height blocks stacked thereon to verify the accuracy of a vertical displacement measurement device associated with the Hamburg Wheel Tracker device.

17. The system of claim 16 wherein:
    the frame comprises a lower flat surface, an upper flat surface, and a ramp extending upwardly from the lower flat surface to the upper flat surface;
    the plurality of height blocks comprise:
      a first height block comprising upper and lower flat surfaces and an inclined end surface extending between the upper and lower surfaces; and
      a second height block comprising upper and lower flat surfaces and an inclined end surface extending between the upper and lower surfaces;
    wherein the plurality of height blocks are configured to be stacked on the frame with the lower surface of the first height block abutting the lower flat surface of the frame, the end surface of the first height block abutting and/or adjacent the ramp, the second height block on the first height block, and with the end surface of the second height block and the upper flat surface of the frame defining an obtuse angle therebetween.

18. The system of claim 17, further comprising a third height block comprising upper and lower flat surfaces and an inclined end surface extending between the upper and lower surfaces;
    wherein the plurality of height blocks are configured to be stacked on the frame with the lower surface of the third height block abutting the upper surface of the first height block and with the end surface of the third height block abutting and/or adjacent the ramp.

19. The system of claim 18, further comprising a fourth height block comprising upper and lower flat surfaces and an inclined end surface extending between the upper and lower surfaces;
    wherein the plurality of height blocks are configured to be stacked on the frame with the lower surface of the fourth height block abutting the upper surface of the second height block and with the end surfaces of the second and fourth height blocks defining a ramp that extends upwardly from the upper flat surface of the frame to the upper surface of the fourth height block.

20. The system of claim 17 further comprising a precision pad, wherein each height block comprises a precision pad receiving feature in an upper surface thereof for receiving and holding the precision pad therein, and wherein the precision pad extends above the upper surface when the precision pad is received in the precision pad receiving feature.

* * * * *